United States Patent
Li et al.

(10) Patent No.: US 8,071,099 B2
(45) Date of Patent: Dec. 6, 2011

(54) ANTI-FLT3 ANTIBODIES

(75) Inventors: Yiwen Li, Jersey City, NJ (US); Dan Lu, Montvale, NJ (US); David Surguladze, Chatham, NJ (US); James Robert Tonra, Skillman, NJ (US)

(73) Assignee: ImClone, LLC, New York, NY (US)

( * ) Notice: Subject to any disclaimer, the term of this patent is extended or adjusted under 35 U.S.C. 154(b) by 0 days.

(21) Appl. No.: 12/890,793

(22) Filed: Sep. 27, 2010

(65) Prior Publication Data
US 2011/0008355 A1   Jan. 13, 2011

Related U.S. Application Data

(63) Continuation of application No. 12/473,295, filed on May 28, 2009, now abandoned.

(60) Provisional application No. 61/130,395, filed on May 30, 2008, provisional application No. 61/130,539, filed on May 30, 2008, provisional application No. 61/130,394, filed on May 30, 2008.

(51) Int. Cl.
*A61K 39/395* (2006.01)
*A61K 39/00* (2006.01)
*C07K 16/24* (2006.01)
*C12N 5/10* (2006.01)

(52) U.S. Cl. ............ 424/145.1; 424/130.1; 424/139.1; 424/141.1; 435/69.1; 435/325; 435/326; 435/331; 530/387.9; 530/388.1; 530/388.23

(58) Field of Classification Search ............... None
See application file for complete search history.

(56) References Cited

U.S. PATENT DOCUMENTS

| | | | |
|---|---|---|---|
| 4,946,778 | A | 8/1990 | Ladner et al. |
| 5,548,065 | A | 8/1996 | Lemischka |
| 5,635,388 | A | 6/1997 | Bennett et al. |
| 5,777,084 | A | 7/1998 | Buhring |
| 6,156,882 | A | 12/2000 | Buhring et al. |
| 6,217,866 | B1 | 4/2001 | Schlessinger et al. |

FOREIGN PATENT DOCUMENTS

| | | |
|---|---|---|
| EP | 322424 | 9/1989 |
| WO | 88/09344 | 12/1988 |
| WO | 89/09622 | 10/1989 |
| WO | 92/01047 | 1/1992 |
| WO | 92/17486 | 10/1992 |
| WO | 93/11236 | 6/1993 |
| WO | 93/21319 | 10/1993 |
| WO | 94/28391 | 12/1994 |
| WO | 95/07348 | 3/1995 |
| WO | 95/27062 | 10/1995 |
| WO | 98/25457 | 6/1998 |
| WO | 99/60023 | 11/1999 |
| WO | 02/102854 | 12/2002 |
| WO | 02/102973 | 12/2002 |
| WO | 05/094823 | 10/2005 |
| WO | 07/124221 | 11/2007 |
| WO | 08/153926 | 12/2008 |

OTHER PUBLICATIONS

U.S. Appl. No. 07/679,666, filed Apr. 2, 1991, Lemischka; The Trustees of Princeton University.
Batley, et al., Life Sci. 62:143-150 (1998).
Burdon, et al., Eds., Laboratory Techniques in Biochemistry and Molecular Biology, vol. 13, Elsevier Science Publishers, Amsterdam (1985); Campbell, Monoclonal Antibody Technology, The Production and Characterization of Rodent and Human Hybridomas.
Burtrum, et al., Cancer Res. 63:8912-21 (2003).
Chothia, et al., J. Mol. Biol. 196 (4):901-917 (1987).
Coligan, et al. Current Protocols in Immunology, Wiley & Sons, Incorporated (1991).
Collins, Glia. 15:289-296 (1995).
Furukawa, et al. Leukemia 21:1005-1014 (2007).
Grandis, et al., Cancer 78:1284-1292 (1996).
Hawkins, et al., J. Mol. Biol. 226:889-896 (1992).
Hermentin, et al., Behring Inst. Mitt. 82:197-215 (1988).
Hoffmann, et al., Anticancer Res. 17:4419-4426 (1997).
Huse, et al., Science 246:1275-1281 (1989).
Jones, Genetics 85:23-33 (1977).
Kabat, et al., Ann. NY Acad. Sci. 190:382-393 (1971).
Kabat, et al., Sequences of Proteins of Immunological Interest, Fifth Edition, U.S. Department of Health and Human Services, NIH Publication No. 91-3242 (1991).
Kaufmann, et al., J. Mol. Biol. 159:601-621 (1982).
Kingsman, et al., Gene 7:141-151 (1979).
Kohler, et al., Nature 256:495-497 (1975).
Lamoyi, et al., J. Immunol. Methods 56:235-243 (1983).
Li, et al., Blood 104(4):1137-1144 (2004).
Li, et al., Drug Devel. Res. 67(6):495-500 (2006).
Li, et al., Expert Opin. Biol. Ther. 7(3):319-330 (2007).
Li, et al., Int. J. Hematol. 82(2):108-114 (2005).
Low, et al., J. Mol. Biol. 250:359-368 (1996).
Nielsen, et al., Prot. Eng. 10:1-6 (1997).
Panek, et al., J. Pharmacol. Exp. Thera. 283:1433-1444 (1997).
Parham, J. Immunol. 131: 2895-2902 (1983).
Pearson, et al., Proc. Natl. Acad. Sci. USA 85:2444-2448 (1988).
Pedley, et al., Br. J. Cancer 68:69-73 (1993).
Petrides, et al., Cancer Res. 50:3934-3939 (1990).
Piloto, et al., Blood 109(4):1643-1652 (2007).
Piloto, et al., Cancer Res. 65(4):1514-1522 (2005).
Piloto, et al., Cancer Res. 66(9):4843-4851 (2006).
Radinsky, et al., Clin. Cancer Res. 1:19-31 (1995).
Sambrook, et al., Molecular Cloning: A Laboratory Manual, 2nd ed., Cold Spring Harbor Laboratory Press (1989).
Sauter, et al., Am. J. Path. 148:1047-1053 (1996).
Scahill, et al., Proc. Nat'l Acad. Sci. 80:4654-4659 (1983).
Shimizu, et al., Japan J. Cancer Res. 85:567-571 (1994).
Shokri, et al., Appl Microbiol Biotechnol. 60:654-664 (2003).
Southern, et al., J. Mol. Appl. Genet. 1:327-341 (1982).
Stincomb, et al., Nature 282:39-43 (1979).
Stirewalt, et al., Nature Reviews Cancer 3:650-665 (2003).

(Continued)

Primary Examiner — Christine J Saoud
Assistant Examiner — Jon M Lockard
(74) Attorney, Agent, or Firm — Nicole S. Woods

(57) ABSTRACT

The present invention provides fully human antibodies that specifically bind to human FLT3 within extracellular domains 4 or 5 with high affinity. The invention further provides methods of treating leukemia by administering an effective amount of an antibody either alone or in combination with an anti-cancer agent or treatment including methotrexate.

26 Claims, No Drawings

OTHER PUBLICATIONS

Subramani, et al., Mol. Cell. Biol. 1:854-864 (1981).
Urlaub, et al., Proc. Nat'l Acad. Sci. 77:4216-4220 (1980).
Von Heinje, et al., Nucl. Acids Res. 14:4683-4690 (1986).
Wikstrand, et al., Cancer Res. 55:3140-3148 (1995).
Williams, et al., AACR annual meeting 2007 poster presented.
Williams, et al., Leukemia 19(8):1432-1438 (2005).
Yang, et al., J. Mol. Biol. 254:392-403 (1995).
Zheng, et al., Blood 103(1):267-274 (2004).
Relevant ClinicalTrials.gov information (last updated Feb. 8, 2011). http://www.clinicaltrials.gov/ct2/show/NCT00887926?term=EB10&rank=1.

SEQUENCE LISTING

```
<160> NUMBER OF SEQ ID NOS: 43

<210> SEQ ID NO 1
<211> LENGTH: 10
<212> TYPE: PRT
<213> ORGANISM: Homo sapiens

<400> SEQUENCE: 1

Gly Tyr Thr Phe Thr Ser Tyr Tyr Met His
1               5                   10

<210> SEQ ID NO 2
<211> LENGTH: 5
<212> TYPE: PRT
<213> ORGANISM: Homo sapiens

<400> SEQUENCE: 2

Ser Tyr Tyr Met His
1               5

<210> SEQ ID NO 3
<211> LENGTH: 17
<212> TYPE: PRT
<213> ORGANISM: Homo sapiens

<400> SEQUENCE: 3

Ile Ile Asn Pro Ser Gly Gly Ser Thr Ser Tyr Ala Gln Lys Phe Gln
1               5                   10                  15

Gly

<210> SEQ ID NO 4
<211> LENGTH: 10
<212> TYPE: PRT
```

-continued

<213> ORGANISM: Homo sapiens

<400> SEQUENCE: 4

Gly Val Gly Ala His Asp Ala Phe Asp Ile
1               5                   10

<210> SEQ ID NO 5
<211> LENGTH: 9
<212> TYPE: PRT
<213> ORGANISM: Homo sapiens

<400> SEQUENCE: 5

Val Val Ala Ala Ala Val Ala Asp Tyr
1               5

<210> SEQ ID NO 6
<211> LENGTH: 16
<212> TYPE: PRT
<213> ORGANISM: Homo sapiens

<400> SEQUENCE: 6

Arg Ser Ser Gln Ser Leu Leu His Ser Asn Gly Asn Asn Tyr Leu Asp
1               5                   10                  15

<210> SEQ ID NO 7
<211> LENGTH: 16
<212> TYPE: PRT
<213> ORGANISM: Homo sapiens

<400> SEQUENCE: 7

Arg Ser Ser Gln Ser Leu Leu His Ser Asn Gly Tyr Asn Tyr Leu Asp
1               5                   10                  15

<210> SEQ ID NO 8
<211> LENGTH: 7
<212> TYPE: PRT
<213> ORGANISM: Homo sapiens

<400> SEQUENCE: 8

Leu Gly Ser Asn Arg Ala Ser
1               5

<210> SEQ ID NO 9
<211> LENGTH: 9
<212> TYPE: PRT
<213> ORGANISM: Homo sapiens

<400> SEQUENCE: 9

Met Gln Gly Thr His Pro Ala Ile Ser
1               5

<210> SEQ ID NO 10
<211> LENGTH: 9
<212> TYPE: PRT
<213> ORGANISM: Homo sapiens

<400> SEQUENCE: 10

Met Gln Gly Thr His Pro Ala Ile Ser
1               5

<210> SEQ ID NO 11
<211> LENGTH: 9
<212> TYPE: PRT
<213> ORGANISM: Homo sapiens

<400> SEQUENCE: 11

Met Gln Ser Leu Gln Thr Pro Phe Thr
1               5

<210> SEQ ID NO 12
<211> LENGTH: 10
<212> TYPE: PRT
<213> ORGANISM: Homo sapiens

<400> SEQUENCE: 12

Gly Gly Thr Phe Ser Ser Tyr Ala Ile Ser
1               5                   10

<210> SEQ ID NO 13
<211> LENGTH: 5
<212> TYPE: PRT
<213> ORGANISM: Homo sapiens

<400> SEQUENCE: 13

Ser Tyr Ala Ile Ser
1               5

<210> SEQ ID NO 14
<211> LENGTH: 17
<212> TYPE: PRT
<213> ORGANISM: Homo sapiens

<400> SEQUENCE: 14

Gly Ile Ile Pro Ile Phe Gly Thr Ala Asn Tyr Ala Gln Lys Phe Gln
1               5                   10                  15

Gly

<210> SEQ ID NO 15
<211> LENGTH: 13
<212> TYPE: PRT
<213> ORGANISM: Homo sapiens

<400> SEQUENCE: 15

Phe Ala Leu Phe Gly Phe Arg Glu Gln Ala Phe Asp Ile
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Ser Ile Ser Ser Tyr Leu Asn
1               5                   10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
1               5

<210> SEQ ID NO 18
<211> LENGTH: 9
<212> TYPE: PRT
<213> ORGANISM: Homo sapiens

<400> SEQUENCE: 18

-continued

Gln Gln Ser Tyr Ser Thr Pro Phe Thr
1               5

<210> SEQ ID NO 19
<211> LENGTH: 119
<212> TYPE: PRT
<213> ORGANISM: Homo sapiens

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Ala His Asp Ala Phe Asp Ile Trp Gly Gln Gly
            100                 105                 110

Thr Thr Val Thr Val Ser Ser
        115

<210> SEQ ID NO 20
<211> LENGTH: 122
<212> TYPE: PRT
<213> ORGANISM: Homo sapiens

<400> SEQUENCE: 20

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Ala Leu Phe Gly Phe Arg Glu Gln Ala Phe Asp Ile Trp
            100                 105                 110

Gly Gln Gly Thr Thr Val Thr Val Ser Ser
        115                 120

<210> SEQ ID NO 21
<211> LENGTH: 118
<212> TYPE: PRT
<213> ORGANISM: Homo sapiens

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Ala Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Val Ala Ala Val Ala Asp Tyr Trp Gly Gln Gly Thr
            100                 105                 110

Leu Val Thr Val Ser Ser
            115

<210> SEQ ID NO 22
<211> LENGTH: 112
<212> TYPE: PRT
<213> ORGANISM: Homo sapiens

<400> SEQUENCE: 22

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Asp Thr Asp Phe Thr Leu Gln Ile
65                  70                  75                  80

Ser Arg Val Glu Ala Glu Asp Val Gly Val Tyr Tyr Cys Met Gln Gly
                85                  90                  95

Thr His Pro Ala Ile Ser Phe Gly Gln Gly Thr Arg Leu Glu Ile Lys
            100                 105                 110

<210> SEQ ID NO 23
<211> LENGTH: 107
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 24
<211> LENGTH: 112

```
<212> TYPE: PRT
<213> ORGANISM: Homo sapiens

<400> SEQUENCE: 24

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Thr Pro Phe Thr Phe Gly Pro Gly Thr Lys Val Asp Ile Lys
            100                 105                 110

<210> SEQ ID NO 25
<211> LENGTH: 449
<212> TYPE: PRT
<213> ORGANISM: Homo sapiens

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Gly Ala His Asp Ala Phe Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 26
<211> LENGTH: 452
<212> TYPE: PRT
<213> ORGANISM: Homo sapiens

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Ala Leu Phe Gly Phe Arg Glu Gln Ala Phe Asp Ile Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 27
<211> LENGTH: 448
<212> TYPE: PRT
<213> ORGANISM: Homo sapiens

<400> SEQUENCE: 27

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Ala Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
```

```
Ala Arg Val Val Ala Ala Val Ala Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 28
<211> LENGTH: 219
<212> TYPE: PRT
<213> ORGANISM: Homo sapiens

<400> SEQUENCE: 28

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
```

```
Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Asp Thr Asp Phe Thr Leu Gln Ile
 65                  70                  75                  80

Ser Arg Val Glu Ala Glu Asp Val Gly Val Tyr Tyr Cys Met Gln Gly
                 85                  90                  95

Thr His Pro Ala Ile Ser Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 214
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Ser Tyr Ser Thr Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 30
<211> LENGTH: 219
<212> TYPE: PRT
<213> ORGANISM: Homo sapiens

<400> SEQUENCE: 30

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Thr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 468
<212> TYPE: PRT
<213> ORGANISM: Homo sapiens

<400> SEQUENCE: 31

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Met His Trp Val Arg Gln Ala Pro Gly Gln Gly Leu
    50                  55                  60

Glu Trp Met Gly Ile Ile Asn Pro Ser Gly Gly Ser Thr Ser Tyr Ala
65                  70                  75                  80

```
Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Val Gly Ala His Asp Ala Phe Asp Ile Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 32
<211> LENGTH: 471
<212> TYPE: PRT
<213> ORGANISM: Homo sapiens
```

<400> SEQUENCE: 32

```
Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Thr Phe Ala Leu Phe Gly Phe Arg Glu Gln Ala Phe
        115                 120                 125

Asp Ile Trp Gly Gln Gly Thr Thr Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 33
<211> LENGTH: 467
<212> TYPE: PRT
<213> ORGANISM: Homo sapiens

<400> SEQUENCE: 33

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Met His Trp Ala Arg Gln Ala Pro Gly Gln Gly Leu
    50                  55                  60

Glu Trp Met Gly Ile Ile Asn Pro Ser Gly Gly Ser Thr Ser Tyr Ala
65                  70                  75                  80

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Val Val Ala Ala Val Ala Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

Arg Val Val Ser Val Leu Thr Val Leu His Gln Asp Trp Leu Asn Gly
             325                 330                 335

Lys Glu Tyr Lys Cys Lys Val Ser Asn Lys Ala Leu Pro Ala Pro Ile
             340                 345                 350

Glu Lys Thr Ile Ser Lys Ala Lys Gly Gln Pro Arg Glu Pro Gln Val
             355                 360                 365

Tyr Thr Leu Pro Pro Ser Arg Glu Glu Met Thr Lys Asn Gln Val Ser
370                     375                 380

Leu Thr Cys Leu Val Lys Gly Phe Tyr Pro Ser Asp Ile Ala Val Glu
385                     390                 395                 400

Trp Glu Ser Asn Gly Gln Pro Glu Asn Asn Tyr Lys Thr Thr Pro Pro
             405                 410                 415

Val Leu Asp Ser Asp Gly Ser Phe Phe Leu Tyr Ser Lys Leu Thr Val
             420                 425                 430

Asp Lys Ser Arg Trp Gln Gln Gly Asn Val Phe Ser Cys Ser Val Met
             435                 440                 445

His Glu Ala Leu His Asn His Tyr Thr Gln Lys Ser Leu Ser Leu Ser
             450                 455                 460

Pro Gly Lys
465

<210> SEQ ID NO 34
<211> LENGTH: 238
<212> TYPE: PRT
<213> ORGANISM: Homo sapiens

<400> SEQUENCE: 34

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
             20                  25                  30

Thr Pro Gly Glu Pro Ala Ser Ile Ser Cys Arg Ser Ser Gln Ser Leu
             35                  40                  45

Leu His Ser Asn Gly Asn Asn Tyr Leu Asp Trp Tyr Leu Gln Lys Pro
     50                  55                  60

Gly Gln Ser Pro Gln Leu Leu Ile Tyr Leu Gly Ser Asn Arg Ala Ser
65                  70                  75                  80

Gly Val Pro Asp Arg Phe Ser Gly Ser Gly Ser Asp Thr Asp Phe Thr
                 85                  90                  95

Leu Gln Ile Ser Arg Val Glu Ala Glu Asp Val Gly Val Tyr Tyr Cys
                100                 105                 110

Met Gln Gly Thr His Pro Ala Ile Ser Phe Gly Gln Gly Thr Arg Leu
             115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
             180                 185                 190

Lys Asp Ser Thr Tyr Ser Leu Ser Ser Thr Leu Thr Leu Ser Lys Ala
             195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 35
<211> LENGTH: 233
<212> TYPE: PRT
<213> ORGANISM: Homo sapiens

<400> SEQUENCE: 35

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Ser Ile
            35                  40                  45

Ser Ser Tyr Leu Asn Trp Tyr Gln Gln Lys Pro Gly Lys Ala Pro Lys
        50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Leu Ala Thr Tyr Tyr Cys Gln Gln Ser Tyr Ser
                100                 105                 110

Thr Pro Phe Thr Phe Gly Pro Gly Thr Lys Val Asp Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 36
<211> LENGTH: 238
<212> TYPE: PRT
<213> ORGANISM: Homo sapiens

<400> SEQUENCE: 36

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Leu His Ser Asn Gly Tyr Asn Tyr Leu Asp Trp Tyr Leu Gln Lys Pro
        50                  55                  60

Gly Gln Ser Pro Gln Leu Leu Ile Tyr Leu Gly Ser Asn Arg Ala Ser
65                  70                  75                  80

```
Gly Val Pro Asp Arg Phe Ser Gly Ser Gly Thr Asp Phe Thr
            85                  90                  95
Leu Lys Ile Ser Arg Val Glu Ala Glu Asp Val Gly Val Tyr Tyr Cys
            100                 105                 110
Met Gln Ser Leu Gln Thr Pro Phe Thr Phe Gly Pro Gly Thr Lys Val
            115                 120                 125
Asp Ile Lys Arg Thr Val Ala Ala Pro Ser Val Phe Ile Phe Pro Pro
            130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
            195                 200                 205
Asp Tyr Glu Lys His Lys Val Tyr Ala Cys Glu Val Thr His Gln Gly
            210                 215                 220
Leu Ser Ser Pro Val Thr Lys Ser Phe Asn Arg Gly Glu Cys
225                 230                 235

<210> SEQ ID NO 37
<211> LENGTH: 1407
<212> TYPE: DNA
<213> ORGANISM: Homo sapiens

<400> SEQUENCE: 37
atgggatggt catgtatcat ccttttttcta gtagcaactg caactggagt acattcagag      60
gtccagctgg tgcagtctgg ggctgaggtg aagaagcctg ggcctcagt gaaggtttcc     120 tgcaaggcat ctggatacac cttcaccagc tactatatgc actgggtgcg acaggcccct     180
ggacaagggc ttgagtggat gggaataatc aaccctagtg gtggtagcac aagctacgca     240
cagaagttcc agggcagagt caccatgacc agggacacgt ccacgagcac agtctacatg     300
gagctgagca gcctgagatc tgaggacacg gccgtgtatt actgtgcgag gggagtggga     360
gcgcatgatg cttttgatat ctggggccaa gggaccacgg tcaccgtctc aagcgctagc     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca agagagttga gcccaaatct     720
tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtatgtg     900
gacggcgtgg aggtgcataa tgccaagaca aagccgcggg aggagcagta caacagcacg     960
taccgtgtgg tcagcgtcct caccgtcctg caccaagact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccaag tcagcctgac ctgcctggtc aaaggcttct atcccagcga catcgccgtg    1200
gagtgggaga gcaatgggca gccggagaac aactacaaga ccacgcctcc cgtgctggac    1260
```

| | |
|---|---|
| tccgacggct ccttcttcct ctattccaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg caaatga | 1407 |

<210> SEQ ID NO 38
<211> LENGTH: 1416
<212> TYPE: DNA
<213> ORGANISM: Homo sapiens

<400> SEQUENCE: 38

| | |
|---|---|
| atgggatggt catgtatcat ccttttttcta gtagcaactg caactggagt acattcagag | 60 |
| gtccagctgg tacagtctgg ggctgaggtg aagaagcctg gtcctcggt gaaggtctcc | 120 |
| tgcaaggctt ctggaggcac cttcagcagc tatgctatca gctgggtgcg acaggcccct | 180 |
| ggacaagggc ttgagtggat gggagggatc atccctatct ttggtacagc aaactacgca | 240 |
| cagaagttcc agggcagagt cacgattacc gcggacaaat ccacgagcac agcctacatg | 300 |
| gagctgagca gcctgagatc tgaggacacg gccgtgtatt actgtgcaac atttgcgctt | 360 |
| ttcgggttca gggagcaggc ttttgatatc tggggccaag ggaccacggt caccgtctca | 420 |
| agcgctagca ccaagggccc atcggtcttc cccctggcac cctcctccaa gagcacctct | 480 |
| gggggcacag cggccctggg ctgcctggtc aaggactact ccccgaaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gagagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca cctcatgat ctcccggacc | 840 |
| cctgaggtca catgcgtggt ggtgacgtg agccacgaag accctgaggt caagttcaac | 900 |
| tggtatgtgg acggcgtgga ggtgcataat gccaagacaa agccgcggga ggagcagtac | 960 |
| aacagcacgt accgtgtggt cagcgtcctc accgtcctgc accagactg gctgaatggc | 1020 |
| aaggagtaca agtgcaaggt ctccaacaaa gccctcccag cccccatcga gaaaaccatc | 1080 |
| tccaaagcca agggcagccc cgagaaccca ggtgtaca ccctgccccc atcccgggag | 1140 |
| gagatgacca agaaccaagt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tattccaagc tcaccgtgga caagagcagg | 1320 |
| tggcagcagg ggaacgtctt ctcatgctcc gtgatgcatg aggctctgca caaccactac | 1380 |
| acgcagaaga gcctctccct gtctccgggc aaatga | 1416 |

<210> SEQ ID NO 39
<211> LENGTH: 1404
<212> TYPE: DNA
<213> ORGANISM: Homo sapiens

<400> SEQUENCE: 39

| | |
|---|---|
| atgggatggt catgtatcat ccttttttcta gtagcaactg caactggagt acattcagag | 60 |
| gtccagctgg tgcagtctgg ggctgaggtg aagaagcctg gggcctcagt gaaggtttcc | 120 |
| tgcaaggcat ctggatacac cttcaccagc tactatatgc actgggcgcg acaggcccct | 180 |
| ggacaagggc ttgagtggat gggaataatc aaccctagtg gtggtagcac aagctacgca | 240 |
| cagaagttcc agggcagagt caccatgacc agggacacgt ccacgagcac agtctacatg | 300 |

| | |
|---|---|
| gagctgagca gcctgagatc tgaggacacg gccgtgtatt actgtgctag agtggtagca | 360 |
| gcagctgttg ccgactactg gggccaggga accctggtca ccgtctcaag cgctagcacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga gagttgagcc caaatcttgt | 720 |
| gacaaaactc acacatgccc accgtgccca gcacctgaac tcctgggggg accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtatgtggac | 900 |
| ggcgtggagg tgcataatgc caagacaaag ccgcgggagg agcagtacaa cagcacgtac | 960 |
| cgtgtggtca gcgtcctcac cgtcctgcac caagactggc tgaatggcaa ggagtacaag | 1020 |
| tgcaaggtct ccaacaaagc cctcccagcc cccatcgaga aaaccatctc caaagccaaa | 1080 |
| gggcagcccc gagaaccaca ggtgtacacc ctgcccccat cccgggagga tgaccaag | 1140 |
| aaccaagtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta ttccaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggcaa atga | 1404 |

<210> SEQ ID NO 40
<211> LENGTH: 717
<212> TYPE: DNA
<213> ORGANISM: Homo sapiens

<400> SEQUENCE: 40

| | |
|---|---|
| atgggatggt catgtatcat cctttttcta gtagcaactg caactggagt acattcagat | 60 |
| gttgtgatga ctcagtctcc actctccctg cccgtcaccc ctggagagcc ggcctccatc | 120 |
| tcctgcaggt ctagtcagag cctcctgcat agtaatggaa acaactattt ggattggtac | 180 |
| ctgcagaagc cagggcagtc tccacagctc ctgatctatt tgggttctaa tcgggcctct | 240 |
| ggggtcccag acagattcag cggcagtggg tcagacactg atttcacact gcaaatcagt | 300 |
| agggtggagg ctgaggatgt tggggtttat tactgcatgc aagtacaca ccccgccatc | 360 |
| tccttcggcc aagggacacg actggagatt aaacgtacgg tggctgcacc atctgtcttc | 420 |
| atcttcccgc catctgatga gcagttgaaa tctggaactg cctctgttgt gtgcctgctg | 480 |
| aataacttct atcccagaga ggccaaagta cagtggaagg tggataacgc cctccaatcg | 540 |
| ggtaactccc aggagagtgt cacagagcag gacagcaagg acagcaccta cagcctcagc | 600 |
| agcaccctga cgctgagcaa agcagactac gagaaacaca aagtctacgc ctgcgaagtc | 660 |
| acccatcagg gcctgagctc gcccgtcaca aagagcttca caggggaga gtgttag | 717 |

<210> SEQ ID NO 41
<211> LENGTH: 702
<212> TYPE: DNA
<213> ORGANISM: Homo sapiens

<400> SEQUENCE: 41

| | |
|---|---|
| atgggatggt catgtatcat cctttttcta gtagcaactg caactggagt acattcagac | 60 |

```
atccagatga cccagtctcc atcctccctg tctgcatctg taggagacag agtcaccatc    120
acttgccggg caagtcagag cattagcagc tatttaaatt ggtatcagca gaaaccaggg    180
aaagccccta agctcctgat ctatgctgca tccagtttgc aagtgggggt cccatcaagg    240
ttcagtggca gtggatctgg gacagatttc actctcacca tcagcagtct gcaacctgaa    300
gatttagcaa catattactg tcaacagagt tacagtaccc cattcacttt cggccctggg    360
accaaagtgg atatcaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                       702

<210> SEQ ID NO 42
<211> LENGTH: 717
<212> TYPE: DNA
<213> ORGANISM: Homo sapiens

<400> SEQUENCE: 42
atgggatggt catgtatcat cctttttcta gtagcaactg caactggagt acattcagat     60
gttgtgatga ctcagtctcc actctccctg cccgtcaccc ctggagagcc ggcctccatc    120
tcctgcaggt ctagtcagag cctcctgcat agtaatggat acaactattt ggattggtac    180
ctgcagaagc cagggcagtc tccacagctc ctgatctatt tgggttctaa tcgggcctcc    240
ggggtccctg acaggttcag tggcagtgga tcaggcacag attttacact gaaaatcagc    300
agagtggagg ctgaggatgt tggggtttat tactgcatgc aatctctaca aaccccattc    360
actttcggcc ctgggaccaa agtggatatc aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca caggggaga gtgttag       717

<210> SEQ ID NO 43
<211> LENGTH: 993
<212> TYPE: PRT
<213> ORGANISM: Homo sapiens

<400> SEQUENCE: 43
```

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

```
Ala Pro Gly Asn Ile Ser Cys Leu Trp Val Phe Lys His Ser Ser Leu
            100                 105                 110
Asn Cys Gln Pro His Phe Asp Leu Gln Asn Arg Gly Val Val Ser Met
        115                 120                 125
Val Ile Leu Lys Met Thr Glu Thr Gln Ala Gly Glu Tyr Leu Leu Phe
130                 135                 140
Ile Gln Ser Glu Ala Thr Asn Tyr Thr Ile Leu Phe Thr Val Ser Ile
145                 150                 155                 160
Arg Asn Thr Leu Leu Tyr Thr Leu Arg Arg Pro Tyr Phe Arg Lys Met
                165                 170                 175
Glu Asn Gln Asp Ala Leu Val Cys Ile Ser Ser Val Pro Glu Pro
            180                 185                 190
Ile Val Glu Trp Val Leu Cys Asp Ser Gln Gly Glu Ser Cys Lys Glu
        195                 200                 205
Glu Ser Pro Ala Val Val Lys Lys Glu Lys Val Leu His Glu Leu
    210                 215                 220
Phe Gly Thr Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
        275                 280                 285
Asn Lys Ala Leu Glu Glu Gly Asn Tyr Phe Glu Met Ser Thr Tyr Ser
    290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Glu Lys Gly Phe Ile Asn Ala
            340                 345                 350
Thr Asn Ser Ser Glu Asp Tyr Glu Ile Asp Gln Tyr Glu Glu Phe Cys
        355                 360                 365
Phe Ser Val Arg Phe Lys Ala Tyr Pro Gln Ile Arg Cys Thr Trp Thr
    370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
        515                 520                 525
```

-continued

```
Leu Asn Ser Pro Gly Pro Phe Pro Phe Ile Gln Asp Asn Ile Ser Phe
    530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
            580                 585                 590
Asp Phe Arg Glu Tyr Glu Tyr Asp Leu Lys Trp Glu Phe Pro Arg Glu
        595                 600                 605
Asn Leu Glu Phe Gly Lys Val Leu Gly Ser Gly Ala Phe Gly Lys Val
    610                 615                 620
Met Asn Ala Thr Ala Tyr Gly Ile Ser Lys Thr Gly Val Ser Ile Gln
625                 630                 635                 640
Val Ala Val Lys Met Leu Lys Glu Lys Ala Asp Ser Ser Glu Arg Glu
                645                 650                 655
Ala Leu Met Ser Glu Leu Lys Met Met Thr Gln Leu Gly Ser His Glu
            660                 665                 670
Asn Ile Val Asn Leu Leu Gly Ala Cys Thr Leu Ser Gly Pro Ile Tyr
        675                 680                 685
Leu Ile Phe Glu Tyr Cys Cys Tyr Gly Asp Leu Leu Asn Tyr Leu Arg
    690                 695                 700
Ser Lys Arg Glu Lys Phe His Arg Thr Trp Thr Glu Ile Phe Lys Glu
705                 710                 715                 720
His Asn Phe Ser Phe Tyr Pro Thr Phe Gln Ser His Pro Asn Ser Ser
                725                 730                 735
Met Pro Gly Ser Arg Glu Val Gln Ile His Pro Asp Ser Asp Gln Ile
            740                 745                 750
Ser Gly Leu His Gly Asn Ser Phe His Ser Glu Asp Glu Ile Glu Tyr
        755                 760                 765
Glu Asn Gln Lys Arg Leu Glu Glu Glu Asp Leu Asn Val Leu Thr
    770                 775                 780
Phe Glu Asp Leu Leu Cys Phe Ala Tyr Gln Val Ala Lys Gly Met Glu
785                 790                 795                 800
Phe Leu Glu Phe Lys Ser Cys Val His Arg Asp Leu Ala Ala Arg Asn
                805                 810                 815
Val Leu Val Thr His Gly Lys Val Val Lys Ile Cys Asp Phe Gly Leu
            820                 825                 830
Ala Arg Asp Ile Met Ser Asp Ser Asn Tyr Val Val Arg Gly Asn Ala
        835                 840                 845
Arg Leu Pro Val Lys Trp Met Ala Pro Glu Ser Leu Phe Glu Gly Ile
    850                 855                 860
Tyr Thr Ile Lys Ser Asp Val Trp Ser Tyr Gly Ile Leu Leu Trp Glu
865                 870                 875                 880
Ile Phe Ser Leu Gly Val Asn Pro Tyr Pro Gly Ile Pro Val Asp Ala
                885                 890                 895
Asn Phe Tyr Lys Leu Ile Gln Asn Gly Phe Lys Met Asp Gln Pro Phe
            900                 905                 910
Tyr Ala Thr Glu Glu Ile Tyr Ile Ile Met Gln Ser Cys Trp Ala Phe
        915                 920                 925
Asp Ser Arg Lys Arg Pro Ser Phe Pro Asn Leu Thr Ser Phe Leu Gly
    930                 935                 940
Cys Gln Leu Ala Asp Ala Glu Glu Ala Met Tyr Gln Asn Val Asp Gly
```

```
                945              950              955              960
Arg Val Ser Glu Cys Pro His Thr Tyr Gln Asn Arg Arg Pro Phe Ser
                    965                  970              975
Arg Glu Met Asp Leu Gly Leu Leu Ser Pro Gln Ala Gln Val Glu Asp
                980                  985              990
Ser
```

ANTI-FLT3 ANTIBODIES

This application is a continuation of U.S. application Ser. No. 12/473,295 filed 28 May 2009 now abandoned, which claims the benefit of U.S. Provisional Application Nos. 61/130,395, 61/130,539, and 61/130,394 all of which were filed May 30, 2008.

The present invention is directed to human antibodies, including fragments or portions thereof, that are specific to human Fms-like tyrosine kinase 3 receptor (FLT3). The antibodies are used for treating growth of cancer cells and can be used alone or in combination with an anti-neoplastic agent, including but not limited to methotrexate (MXT), for treatment of leukemia.

Human Fms-like tyrosine kinase 3 receptor (FLT3), also known as fetal liver kinase 2 (FLK-2), stem cell tyrosine kinase 1 (STK-1) and CD135 (SEQ ID NO: 43), is a member of the class III receptor tyrosine kinases. Normally, FLT3 is expressed on immature myeloid-lymphocytic precursor cells and dendritic cell precursors, but rarely on mature adult cells. FLT3 is overexpressed in approximately 90% of acute myeloid leukemia (AML), a majority of acute lymphocytic leukemia (ALL) and the blast-crisis phase of chronic myeloid leukemia (BC-CML). Stimulation by FLT3 ligand (FL) enhances the proliferation and survival of leukemia cells. Inhibition of FLT3 signaling leads to apoptosis in dendritic cells and inhibition of immune responses.

Small-molecule inhibitors are not completely FLT3-specific and drug resistance can develop. Thus small-molecule FLT3 inhibitors have yet to provide effective targeted therapies for leukemia. New treatments for this unmet medical need are highly desirable. An antibody approach may overcome some of the shortcomings associated with small molecule FLT3 inhibitors. First, antibodies are specific to a defined antigen, thus avoiding potential side effects resulting from inhibition of multiple kinases. Second, FLT3 neutralizing antibodies target the extracellular domain, which is less prone to mutations than the kinase domain, reducing the possibility for drug resistance. Third, antibodies may recruit immune effector mechanisms, such as antibody-dependent cellular cytotoxicity (ADCC) and/or complement-mediated cytotoxicity (CMC), to kill target tumor cells, resulting in increased therapeutic efficacy. Finally, FLT3-specific antibodies can be active against both wild-type (especially in the case of a neutralizing antibody) and mutated FLT3 (due to immune effector mechanisms), broadening the target patient population.

Past efforts regarding development of therapeutics for leukemia including FLT3 inhibitors (Li Y., et al., Int. J. Hematol. 82(2):108-14 (2005), Li Y., Drug Development Research 67(6): 495-500 (2006). Li Y., et al., Expert Opinion in Biological Therapy 7(3): 319-330 (2007.)) have been largely unsuccessful. Other development strategies have included: U.S. Pat. No. 5,777,084 hybridoma antibodies; WO95/27062 agonist antibodies, WO94/28391 antibodies to the ligand; WO2005/094823 small molecules.

Zheng R., et al., Blood 103(1):267-274 (2004), Li Y., et al., Blood 104(4):1137-44 (2004), Piloto, O., et al., Cancer Res. 65(4): 1514-22 (2005), Williams B., et al., Leukemia 19(8): 1432-8 (2005), Piloto O., et al., Cancer Res. 66(9):4843-51 (2006) Piloto O., et al., Blood 109(4): 1643-1652 (2007) and Brent R., et al., AACR Annual Meeting 2007, Los Angeles (2007). disclose human antagonist antibodies with high binding affinity to the FLT3 receptor.

Several anti-FLT3 antibodies, including EB10, NC7 and D4-3, inhibit both ligand-dependent (wild-type receptor) as well as ligand-independent (mutant receptor) activation of FLT3 (see Piloto, Cancer Res., supra.). Until the present invention, the precise CDR sequences and epitope binding domains of anti-FLT3 antibodies of the invention have not been known.

Additionally, there is a need to provide alternative anti-FLT3 inhibitors which have high binding affinity for FLT3 and block the binding of the ligand to the FLT3 receptor, and therefore inhibit the activation of FLT3 and its signaling pathway as compared with those inhibitors known in the art. The present invention seeks to provide alternative anti-FLT3 antibodies which have improved ligand blocking and binding affinity for FLT3 compared with those inhibitors known in the art.

There is also a need to provide alternative anti-FLT3 inhibitors which induce rapid and efficient internalization and down-modulation of cell surface FLT3. The present invention seeks to provide human anti-FLT3 antibodies which induce rapid and efficient internalization and down-modulation of cell surface FLT3 compared with those inhibitors known in the art.

There is also a need to provide alternative anti-FLT3 inhibitors which inhibit FL-induced phosphorylation of wild-type FLT3 and downstream kinases of MPK, PI3K, and STAT5 pathways in leukemia. The present invention seeks to provide human anti-FLT3 antibodies which inhibit FL-induced phosphorylation of wild-type FLT3 and downstream kinases of MPK, PI3K, and STAT5 pathways in leukemia compared with those inhibitors known in the art.

Further, there is a need to provide alternative anti-FLT3 inhibitors which have improved ability to activate downstream immune effector functions such as antibody dependent cellular cytotoxicity (ADCC). The present invention seeks to provide human anti-FLT3 antibodies which have improved ability to activate downstream immune effector functions including ADCC as compared with those inhibitors known in the art.

Fully human or humanized antibodies offer the greatest potential for success as human therapeutics since they would be less immunogenic than murine or chimeric antibodies in humans such as WO95/07348 and WO98/25457. The antibodies of the present invention possess these aforementioned characteristics, thereby providing significant advantages.

Until the present invention, the combination of FLT3 inhibitors with methotrexate (MTX) for the treatment of leukemia has been perceived to have no benefit. This dogma stems from findings reported that a combination of a small molecule FLT3 inhibitor and methotrexate utilizing leukemia cell lines in culture was not effective in treating leukemia, while combinations with other chemotherapies were effective (Furukawa, Y. et al., Leukemia (2007) 21:1005-1014). Experimental results relating to the present invention demonstrate that in fact combining an antibody targeting FLT3, namely EB10, with MTX in an animal model of leukemia results in a dramatic improvement in survival.

The present invention provides an antibody, or fragment thereof, which binds an epitope within domains D4 or D5 of human FLT3.

The present invention provides a method of treating a pre-cancerous condition or cancer in a mammal comprising administering MTX in combination with a FLT3 inhibitor to the mammal in an amount effective to treat the pre-cancerous condition or cancer. The present invention also provides a conjugate comprising a FLT3 inhibitor joined to MTX.

The present invention is directed to human antibodies, and fragments thereof, that bind to the human antigen FLT3 (SEQ ID NO:43) with an affinity no greater than $4.5 \times 10^{-10}$ M for soluble FLT3-Fc fusion protein at 25° C. as determined by surface plasmon resonance. The present invention is also directed to human monoclonal antagonist antibodies, and fragments thereof, that bind to the human antigen FLT3.

One aspect of the present invention is an antibody or fragment thereof that binds FLT3, comprising a CDRH1 having the sequence GYTFTSYYMH (SEQ ID NO:1) or SYYMH (SEQ ID NO:2), a CDRH2 having the sequence IINPSGGSTSYAQKFQG (SEQ ID NO:3), a CDRH3 having the sequence GVGAHDAFDI (SEQ ID NO:4) or VVAAAVADY (SEQ ID NO:5), a CDRL1 having the sequence RSSQSLLHSNGNNYLD (SEQ ID NO:6) or RSSQSLLHSNGYNYLD (SEQ ID NO:7), a CDRL2 having the sequence LGSNRAS (SEQ ID NO:8), and a CDRL3 having the sequence MQGTHPAIS (SEQ ID NO:9) or MQSLQTPFT (SEQ ID NO:11).

One aspect of the present invention is an antibody or fragment thereof that binds FLT3 comprising a CDRH1 having the sequence GYTFTSYYMH (SEQ ID NO:1) or SYYMH (SEQ ID NO:2), a CDRH2 having the sequence IINPSGGSTSYAQKFQG (SEQ ID NO:3), a CDRH3 having the sequence GVGAHDAFDI (SEQ ID NO:4), a CDRL1 having the sequence RSSQSLLHSNGNNYLD (SEQ ID NO:6), a CDRL2 having the sequence LGSNRAS (SEQ ID NO:8), and a CDRL3 having the sequence MQGTHPAIS (SEQ ID NO:9). In yet another aspect, the antibody having the aforementioned CDRs specifically binds human FLT3 with an affinity no greater than $4.5 \times 10^{-10}$ M at 25° C. as determined by surface plasmon resonance.

In another aspect of the present invention, the antibody or fragment thereof that specifically binds FLT3, comprising a CDRH1 having the sequence GYTFTSYYMH (SEQ ID NO:1) or SYYMH (SEQ ID NO:2), a CDRH2 having the sequence IINPSGGSTSYAQKFQG (SEQ ID NO:3), a CDRH3 having the sequence VVAAAVADY (SEQ ID NO:5), a CDRL1 having the sequence RSSQSLLHSNGYNYLD (SEQ ID NO:7), a CDRL2 having the sequence LGSNRAS (SEQ ID NO:8), and a CDRL3 having the sequence MQSLQTPFT (SEQ ID NO:11).

In another aspect of the present invention, the antibody or fragment thereof that specifically binds FLT3, comprising a CDRH1 having the sequence GGTFSSYAIS (SEQ ID NO:12) or SYAIS (SEQ ID NO:13), a CDRH2 having the sequence GIIPIFGTANYAQKFQG (SEQ ID NO:14), a CDRH3 having the sequence FALFGFREQAFDI (SEQ ID NO:15), a CDRL1 having the sequence RASQSISSYLN (SEQ ID NO:16), a CDRL2 having the sequence AASSLQS (SEQ ID NO:17), and a CDRL3 having the sequence QQSYSTPFT (SEQ ID NO:18).

Another aspect of the present invention is an antibody or fragment thereof that binds FLT3, and comprises a VL having the sequence:

(SEQ ID NO: 22)
DVVMTQSPLSLPVTPGEPASISCRSSQSLLHSNGNNYLDWYLQKPGQSPQ

LLIYLGSNRASGVPDRFSGSGSDTDFTLQISRVEAEDVGVYYCMQGTHPA

ISFGQGTRLEIK, and a VH sequence of:

(SEQ ID NO: 19)
EVQLVQSGAEVKKPGASVKVSCKASGYTFTSYYMHWVRQAPGQGLEWMGI

INPSGGSTSYAQKFQGRVTMTRDTSTSTVYMELSSLRSEDTAVYYCARGV

GAHDAFDIWGQGTTVTVSS.

Another aspect of the present invention is an antibody or fragment thereof that binds FLT3, and comprises a VL having the sequence:

(SEQ ID NO: 24)
DVVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQSLQTP

FTFGPGTKVDIK, and a VH sequence of:

(SEQ ID NO: 21)
EVQLVQSGAEVKKPGASVKVSCKASGYTFTSYYMHWARQAPGQGLEWMGI

INPSGGSTSYAQKFQGRVTMTRDTSTSTVYMELSSLRSEDTAVYYCARVV

AAAVADYWGQGTLVTVSS.

Another aspect of the present invention is an antibody or fragment thereof that binds FLT3, and comprises a VL having the sequence:

(SEQ ID NO: 23)
DIQMTQSPSSLSASVGDRVTITCRASQSISSYLNWYQQKPGKAPKLLIYA

ASSLQSGVPSRFSGSGSGTDFTLTISSLQPEDLATYYCQQSYSTPFTFGP

GTKVDIK, and a VH sequence of:

(SEQ ID NO: 20)
EVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCATFA

LFGFREQAFDIWGQGTTVTVSS.

Another aspect of the present invention is a monoclonal antibody comprising a light chain of SEQ ID NO: 28 and a heavy chain of SEQ ID NO: 25; or a light chain of SEQ ID NO: 29 and a heavy chain of SEQ ID NO: 26; or a light chain of SEQ ID NO: 30 and a heavy chain of SEQ ID NO: 27. In another aspect of the present invention, an antibody comprises two light chains of SEQ ID NO: 28 and two heavy chains of SEQ ID NO: 25, or comprises two light chains of SEQ ID NO: 29 and two heavy chains of SEQ ID NO: 26; or comprises two light chains of SEQ ID NO: 30 and two heavy chains of SEQ ID NO: 27. FLT3-binding fragments of such antibodies are part of the invention.

The present invention is also directed to isolated DNA encoding such antibodies and portions thereof. Other aspects of the present invention include: an isolated polynucleic acid comprising a nucleotide sequence encoding the antibody, or a fragment thereof; an expression vector comprising the nucleotide sequence linked to an expression sequence or a recombinant host cell comprising the expression vector or a recombinant host cell or a progeny thereof, wherein the cell expresses the antibody, or fragment thereof. Yet another aspect of the present invention is a method of producing or purifying an antibody, or fragment thereof, comprising culturing the cells under conditions permitting expression of the antibody or fragment thereof.

Additionally, the present invention is directed to methods of inhibiting growth of a cancer cell, and methods of treating leukemia, all in mammals, by administering an effective amount of an antibody. Antibodies of the present invention can be used to treat neoplastic diseases, including solid and non-solid tumors, and for treatment of leukemia. One aspect of the present invention is using the previously described antibodies or fragments thereof as a medicament. In yet another aspect, the previously described antibodies or fragments thereof are to be used in the treatment of cancer, including but not limited to leukemia. The present invention also provides for the use of an antibody of the invention for the manufacture of a medicament for the treatment of cancer. In a preferred embodiment the cancer is leukemia.

The antibodies of the present invention may be used alone or in combination with an anti-neoplastic agent or treatment. One aspect of the present invention is using the previously described antibodies in combination with an additional anti-cancer agent or treatment. In yet another aspect, the anti-cancer agent is methotrexate.

Naturally occurring antibodies typically have two identical heavy chains and two identical light chains with each light chain covalently linked to a heavy chain by an interchain disulfide bond. Multiple disulfide bonds further link the two heavy chains to one another. Engineered antibodies can encompass a variety of alterations to the structure and/or format of naturally occurring antibodies. As used herein, the term "antibody" includes immunoglobulin molecules comprising 4 polypeptide chains, two heavy (H) chains and two light (L) chains inter-connected by disulfide bonds. Individual chains can fold into domains having similar sizes (110-125 amino acids) and structures, but different functions.

The light chain can comprise one variable domain (abbreviated herein as VL) and/or one constant domain (abbreviated herein as CL). The light chains of antibodies (immunoglobulins) are either kappa (K) light chains or lambda (λ) light chains. The expression VL, as used herein, is intended to include both the variable regions from kappa-type light chains (Vκ) and from lambda-type light chains (Vλ). The light chain constant region is comprised of one domain, CL.

The heavy chain can also comprise one variable domain (abbreviated herein as VH) and/or, depending on the class or isotype of antibody, three or four constant domains (CH1, CH2, CH3 and CH4) (abbreviated herein collectively as CH). In humans, the isotypes IgA, IgD, IgE, IgG, and IgM, with IgA and IgG further subdivided into subclasses or subtypes ($IgA_{1-2}$ and $IgG_{1-4}$). The present invention includes antibodies of any of the aforementioned classes or subclasses. Human $IgG_1$ is the preferred isotype for the antibodies of the present invention.

Generally, the variable domains show considerable amino acid sequence variability from one antibody to the next, particularly at the location of the antigen-binding site. Three regions, called hypervariable or complementarity-determining regions (abbreviated herein as CDRs), are found in each of VL and VH, which are supported by less variable regions called frameworks (abbreviated herein as FR). Amino acids are assigned to a particular CDR region or domain in accordance with Kabat convention (Kabat, et al., Ann. NY Acad. Sci. 190:382-93 (1971).; Kabat, et al., Sequences of Proteins of Immunological Interest, Fifth Edition, U.S. Department of Health and Human Services, NIH Publication No. 91-3242 (1991).) or Chothia convention (C. Chothia and A. M. Lesk, J. Mol. Biol. 196 (4): 901-917 (1987).)(A. Martin, http://www.bioinf.org.uk/abs/chothia.html). Each VH and VL is composed of three CDRs and four FRs, arranged from amino-terminus to carboxy-terminus in the following order: FR1-CDR1-FR2-CDR2-FR3-CDR3 -FR4.

The portion of an antibody consisting of VL and VH domains is designated Fv (Fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker (see, e.g., U.S. Pat. No. 4,946,778 (Ladner et al.), WO 88/09344 (Huston et al.), WO 92/01047 (McCafferty et al.)) describes the display of scFv fragments on the surface of soluble recombinant genetic display packages, such as bacteriophage.

The peptide linkers used to produce the single chain antibodies can be flexible peptides selected to assure that the proper three-dimensional folding and association of the VL and VH domains occurs. The linker is generally 10 to 50 amino acid residues. Preferably, the linker is 10 to 30 amino acid residues. More preferably the linker is 12 to 30 amino acid residues. Most preferably is a linker of 15 to 25 amino acid residues. A non-limiting example of such a linker peptides is $(Gly-Gly-Gly-Gly-Ser)_3$.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Contaminant components of its natural environment are materials which would interfere with diagnostic or therapeutic uses for the antibody, and may include enzymes, hormones, and other proteinaceous or non-proteinaceous solutes. Examples of isolated antibodies include an antibody that has been affinity purified, an antibody that has been made by a hybridoma or other cell line in vitro, and a human antibody derived from a transgenic mouse.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "human antibody," as used herein, includes antibodies having variable and constant regions corresponding to human germline immunoglobulin sequences (as described in Kabat, et al., supra and Chothia et al., supra). The human antibodies of the invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g., an activity enhancing amino acid residue which is not encoded by the human germline immunoglobulin sequence. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences (See, Kabat, et al., supra and Chothia et al., supra).

Fc (Fragment, crystallizable region) is the designation for the portion or fragment of an antibody that consists of paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement-mediated cytotoxicity (CMC) and ADCC. For antibodies such as IgA and IgM, which are complexes of multiple IgG like proteins, complex formation requires Fc constant domains.

Thus, antibodies of the invention include, but are not limited to, naturally occurring antibodies, antibodies, human antibodies, humanized antibodies, recombinant human antibodies, monoclonal antibodies, digestion fragments, specified portions and variants thereof, including antibody mimetics or comprising portions of antibodies that mimic the structure and/or function of an antibody or specified fragment or portion thereof; each containing at least one CDR. Functional fragments include antigen binding fragments that bind to a FLT3 antigen. For example, antibody fragments capable of binding to FLT3 or a portion thereof, and which are embraced by the present invention include bivalent fragments such as (Fab')$_2$ with inter-chain disulfide bonds intact, monovalent fragments such as Fab (Fragment, antigen binding) which refers to the fragments of the antibody consisting of VL-CL VL-CH1 domains and do not retain the heavy chain hinge region (e.g., by papain digestion), fabs which retain the heavy chain hinge region, facb (e.g., by plasmin digestion), F(ab')$_2$, Fab' which lack disulfide bonds, pFc' (e.g., by pepsin or plasmin digestion), Fd (e.g., by pepsin digestion, partial reduction and re-aggregation) and Fv or scFv (e.g., by molecular biology techniques). Antibody fragments are also intended to include, e.g., domain deleted antibodies, linear antibodies, single chain antibodies, scFv, single domain antibodies, multivalent single chain antibodies, multi-specific antibodies formed from antibody fragments including diabodies, triabodies, and the like that bind specifically with antigens.

The hinge region separates the Fab and Fc portions of the antibody, providing for mobility of Fabs relative to each other and relative to Fc, as well as including multiple disulfide bonds for covalent linkage of the two heavy chains.

Antibody formats have been developed which retain binding specificity, but have other characteristics that may be desirable, including for example, bispecificity, multivalence (more than two binding sites), and compact size (e.g., binding domains alone).

The antibodies of the present invention are specific for FLT3. Antibody specificity refers to selective recognition of the antibody for a particular epitope of an antigen. Antibodies of the present invention, for example, can be monospecific or bispecific. Bispecific antibodies (BsAbs) are antibodies that have two different antigen-binding specificities or sites. Where an antibody has more than one specificity, the recognized epitopes can be associated with a single antigen or with more than one antigen. Thus, the present invention provides bispecific antibodies that bind to two different antigens, with at least one specificity for FLT3. As stated above, such antibodies include any fragments thereof.

Specificity of the present antibodies or fragments thereof, for FLT3 can be determined based on affinity and/or avidity. Affinity, represented by the equilibrium constant for the dissociation of an antigen with an antibody ($K_D$), measures the binding strength between an antigenic determinant and an antibody-binding site.

The antibodies, or fragments thereof, of the invention bind to an epitope of FLT3 which may comprise any one of FLT3's five extracellular domain segments (hereinafter referred simply to as "domains" or "ECD"), i.e, D1, D2, D3, D4 and D5. The epitope to which the antibodies or fragments of the present invention bind is within domain D4 or D5. Antibodies EB10 and D4-3 bind to an epitope within domain 4 of FLT3, whereas NC7 binds to an epitope within domain 5 of FLT3. The term "epitope" as used herein refers to discrete, three-dimensional sites on an antigen that are recognized by the antibodies of the invention. Epitopes are the immunologically active regions on a complex antigen, the regions that actually bind to a B-cell receptor, and that are actually bound by the resulting antibody molecules that are produced by the B cell. Antigens generally contain at least one epitope and usually more than one epitope. Epitopes on protein antigens can be linear or non-linear. Linear epitopes are those comprised of contiguous amino acid residues in the amino acid sequence of a protein. Linear epitopes may or may not require conformational folding to form the native three-dimensional structure and elicit an immune response that produces antibodies with binding specificity to the antigen. Non-linear epitopes are comprised of non-contiguous amino acid residues. Thus, non-linear epitopes require some degree of protein folding to bring the requisite amino acid residues into the proximity of one another to form the native three-dimensional structure and elicit an immune response that produces antibodies with binding specificity to the antigen.

The antibodies, or fragments thereof, of the present invention bind to wild-type or mutant FLT3. FLT3, either mutant or wild-type, for example, is frequently expressed in AML and ALL, as well as other leukemias. It is mutated in about one-third of acute AML patients, either by internal tandem duplications (ITD) of the juxtamembrane domain or by point mutations usually involving the kinase domain (KD). Both types of mutation constitutively activate FLT3. Besides interfering with FLT3 signaling, anti-FLT3 antibodies can also induce ADCC as an additional mechanism for inducing cytotoxicity.

Antibodies of the present invention, or fragments thereof, also include those for which binding characteristics have been modified or improved by direct mutation, methods of affinity maturation, phage display, or chain shuffling. Affinity and specificity can be modified or improved by mutating CDR and/or FW residues and screening for antigen binding sites having the desired characteristics (see, e.g., Yang et al., J. Mol. Biol. 254: 392-403 (1995).). CDRs are mutated in a variety of ways. One way is to randomize individual residues or combinations of residues so that in a population of, otherwise identical antigen binding sites, subsets of from two to twenty amino acids are found at particular positions. Alternatively, mutations can be induced over a range of residues by error prone PCR methods (see, e.g., Hawkins et al., J. Mol. Biol. 226: 889-96 (1992)). In another example, phage display vectors containing heavy and light chain variable region genes can be propagated in mutator strains of *E. coli* (see, e.g., Low et al., J. Mol. Biol. 250: 359-68 (1996).). For example, phage display vectors containing heavy and light chain variable region genes can be propagated in mutator strains of *E.*

*coli* (see, e.g., Low et al., J. Mol. Biol. 250: 359-368 (1996)). These methods of mutagenesis are illustrative of the many methods known to one of skill in the art.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity, specificity, IC50, EC50, $K_D$) as herein disclosed. In order to identify candidate CDR region sites for modification, alanine scanning mutagenesis can be performed to identify CDR region residues contributing significantly to antigen binding. Alternatively, or in addition, random mutagenesis may be performed on one or more CDR sequences at one or more residue positions, either while the CDR is operably linked to the variable region or while the CDR is independent of other variable region sequence and then the altered CDR returned to a variable region using recombinant DNA technology. Once such variant antibodies are generated and expressed, the panel of variants is subjected to screening as described herein and antibodies with superior properties in one or more relevant assays may be selected for further development.

In addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

The present invention includes FLT3-binding polypeptides with amino acid sequences substantially the same as the described amino acid sequence of the variable or hypervariable regions of the full-length anti-FLT3 antibodies. Substantially the same amino acid sequence is defined herein as a sequence with at least 70%, preferably at least about 80%, and more preferably at least about 90% homology to another amino acid sequence, as determined by the FASTA search method in accordance with Pearson and Lipman (Proc. Natl. Acad. Sci. USA 85: 2444-8 (1988).). Additionally, the present invention includes conservative amino acid substitutions that preserve the functional characteristics of the presently disclosed antibodies.

The present invention includes nucleic acid sequences that encode an anti-FLT3 antibody heavy chain, comprising any one of the VH regions or a portion thereof, or any one of the VH CDRs, including any variants thereof, as disclosed herein. The invention also includes nucleic acid molecules that encode an anti-FLT3 antibody light chain comprising any one of the VL regions or a portion thereof or any one of the VL CDRs, including any variants thereof as disclosed herein.

Each domain of the antibodies of this invention can be a complete antibody with the heavy or light chain variable domain, or it can be a functional equivalent or a mutant or derivative of a naturally-occurring domain, or a synthetic domain constructed, for example, in vitro using a technique such as one described in WO 93/11236 (Griffiths, et al.). For instance, it is possible to join together domains corresponding to antibody variable domains, which are missing at least one amino acid. Also included is an antibody with one or more amino acid substitution, mutation or deletion within one of the CDR sequences. The important characterizing feature is the ability of each domain to associate with a complementary domain to form an antigen-binding site. Accordingly, the terms variable heavy and light chain fragment should not be construed to exclude variants, including variants to the CDRs that do not have a material effect on specificity.

The antibodies of the present invention may be produced by methods known in the art. These methods include the immunological method described by Kohler and Milstein, Nature 256: 495-497 (1975) and Campbell, Monoclonal Antibody Technology, The Production and Characterization of Rodent and Human Hybridomas, Burdon et al., Eds., Laboratory Techniques in Biochemistry and Molecular Biology, Volume 13, Elsevier Science Publishers, Amsterdam (1985); as well as by the recombinant DNA method described by Huse et al., Science 246: 1275-1281 (1989). The antibodies can also be obtained from phage display libraries bearing combinations of VH and VL domains in the form of scFv or Fab. The VH and VL domains can be encoded by nucleotides that are synthetic, partially synthetic, or naturally derived. In certain embodiments, phage display libraries bearing human antibody fragments can be preferred. Other sources of human antibodies are transgenic mice engineered to express human immunoglobulin genes.

Antibody fragments can be produced by cleaving a whole antibody, or by expressing DNA that encodes the fragment. Fragments of antibodies may be prepared by methods described by Lamoyi et al., J. Immunol. Methods 56: 235-243 (1983) and by Parham, J. Immunol. 131: 2895-2902 (1983). Such fragments may contain one or both Fab fragments or the F(ab')$_2$ fragment. Such fragments may also contain single-chain fragment variable region antibodies, i.e. scFv, diabodies, or other antibody fragments. Methods of producing such functional equivalents are disclosed in PCT Application WO 93/21319, European Patent Application No. 239,400; PCT Application WO 89/09622; European Patent Application 338,745; and European Patent Application EP 332,424. Throughout this specification, the term "antibodies" of the invention includes any fragments thereof, whether or not specifically stated.

Preferred host cells for transformation of vectors and expression of the antibodies of the present invention are mammalian cells, e.g., NSO cells (non-secreting (0) mouse myeloma cells), 293 and CHO cells and other cell lines of lymphoid origin such as lymphoma, myeloma, or hybridoma cells. Other eukaryotic hosts, such as yeasts, can be alternatively used.

The present invention provides isolated antibodies or fragments thereof specific for FLT3. The antibodies of the invention are capable of one or more of the following activities: 1) displaying high affinity binding towards FLT3; 2) blocking ligand binding to FLT3 receptor and therefore to inhibit the activation of FLT3 and its signaling pathway; 3) inducing rapid and efficient internalization and down-modulation of cell surface FLT3; 4) inhibiting FL-induced phosphorylation of wild-type FLT3 and downstream kinases of MPK, PI3K, and STAT5 pathways in leukemia; 5) displaying reduced immunogenicity in humans; 6) displaying improved ability to activate downstream immune effector functions such as antibody dependent cellular cytotoxicity (ADCC); 7) inducing FLT3 receptor internalization and 8) inhibiting tumor growth in vitro and in vivo. In one aspect of the invention, the anti-FLT3 antibodies of the present invention are human antibodies that exhibit one or more of following properties, further elucidated throughout the specification, including the Examples:

(i) inhibition of FLT3 ligand (FL) binding to wild-type FLT3;
(ii) inhibition of FL binding to internal tandem duplications mutant FLT3 (FLT3 -ITD);
(iii) binding to an epitope within domain 4 and/or domain 5 of FLT3;
(iv) neutralization of FL activation of FLT3;
(v) neutralization of FLT3 activation independent of FL;
(vi) mediation of ADCC;
(vii) internalization of FLT3;
(viii) reduction of surface FLT3; or
(ix) binding to FLT3 with a $K_D$ no greater than about $4.5 \times 10^{-10}$ M.

The antibodies of the present invention bind to the external domain of FLT3 and inhibit binding of FL to FLT3 Inhibition can be determined, for example, by a direct binding assay using purified or membrane bound receptor. In one embodiment, the antibodies of the present invention, or fragments thereof, preferably bind FLT3 at least as strongly as the natural ligands of FLT3.

The antibodies of the present invention neutralize FLT3. Neutralization occurs via a variety of mechanisms. One such mechanism is the binding of a FL to an extracellular domain of FLT3 that stimulates autophosphorylation of the beta subunit and phosphorylation of FLT3 substrates, including STAT5, Akt, PI3K and MAPK which are downstream pathways. Neutralization of FLT3 also includes inhibition, diminution, inactivation and/or disruption of one or more of these activities normally associated with signal transduction. Further, neutralization includes inhibition of FLT3 heterodimers as well as FLT3 homodimers. Accordingly, neutralizing FLT3 has various effects, including inhibition, diminution, inactivation and/or disruption of growth (proliferation and differentiation), angiogenesis (blood vessel recruitment, invasion, and metastasis), and cell motility and metastasis (cell adhesion and invasiveness). By neutralizing FLT3, by way of, but not limited to the various mechanisms disclosed, the antibodies of the present invention decrease FLT3 kinase activity thereby inhibiting disease progression.

One measure of FLT3 neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies in the context of the present invention. Phosphorylation can be detected, for example, using an antibody specific for phosphotyrosine in an ELISA assay or on a Western blot. Some assays for tyrosine kinase activity are described in Panek et al., J. Pharmacol. Exp. Thera. 283:1433-44 (1997) and Batley et al., Life Sci. 62:143-50 (1998). Antibodies of the invention cause a significant decrease in tyrosine phosphorylation of FLT3 of at least about 60%, preferably at least about 75%, and more preferably at least about 85-90% in cells that respond to ligand.

Another measure of FLT3 neutralization is inhibition of phosphorylation of downstream substrates of FLT3. Accordingly, the level of phosphorylation of STAT5, PI3K, Akt or MAPK can be measured.

In addition, methods for detection of protein expression can be utilized to determine FLT3 neutralization, wherein the proteins being measured are regulated by FLT3 tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., Cancer 78:1284-92 (1996); Shimizu et al., Japan J. Cancer Res. 85:567-71 (1994); Sauter et al., Am. J. Path. 148:1047-53 (1996); Collins, Glia 15:289-96 (1995); Radinsky et al., Clin. Cancer Res. 1:19-31 (1995); Petrides et al., Cancer Res. 50:3934-39 (1990); Hoffmann et al., Anticancer Res. 17:4419-26 (1997); Wikstrand et al., Cancer Res. 55:3140-48 (1995).

In vivo assays can also be utilized to determine FLT3 neutralization. For example, receptor tyrosine kinase inhibition can be observed by mitogenic assays using cell lines stimulated with receptor ligand in the presence and absence of inhibitor. One method involves testing for inhibition of growth of FLT3-expressing tumor cells or cells transfected to express FLT3. Inhibition can also be observed using tumor models, for example, human tumor cells injected into a mouse.

The present invention is not limited by any particular mechanism of FLT3 neutralization. The anti-FLT3 antibodies of the present invention can (1) bind externally to the FLT3 cell surface receptor, (2) block binding to FL and subsequent signal transduction mediated via the receptor-associated tyrosine kinase, and (3) prevent phosphorylation of the FLT3 and other downstream proteins in the signal transduction cascade.

In another embodiment, the antibodies of the present invention down-modulate FLT3. The amount of FLT3 present on the surface of a cell depends on receptor protein production, internalization, and degradation. The amount of FLT3 present on the surface of a cell can be measured indirectly, by detecting internalization of the receptor or a molecule bound to the receptor. For example, receptor internalization can be measured by contacting or coating cells that express FLT3 with a labeled antibody. The membrane-bound antibody is then stripped, collected and counted. Internalization of the antibody is determined by lysing the cells and detecting the labeled components.

The amount of FLT3 present on the surface of a cell can be measured directly by measuring the amount of the receptor present on the cell following treatment with an anti-FLT3 antibody or other substance, for example, by fluorescence-activated cell-sorting analysis of cells stained for surface expression of FLT3. Stained cells are incubated and fluorescence intensity measured over time. As a control, part of the stained population can be incubated at conditions under which receptor internalization is halted.

As described in the Examples below, cell surface FLT3 can be detected and measured using a different antibody that is specific for FLT3 and that does not block or compete with binding of the antibody being tested. (Burtrum, et al., Cancer Res. 63:8912-21 (2003)). In one embodiment, treatment of an FLT3 expressing cell with an antibody of the present invention results in reduction of cell surface FLT3.

Another measure of down-modulation is reduction of the total receptor protein present in a cell, and reflects degradation of internal receptors. Accordingly, treatment of cells (particularly cancer cells) with antibodies of the invention results in a significant reduction in total cellular FLT3.

The antibodies of the present invention inhibit tumor growth. For example, subcutaneous xenograft tumors can be established by injection of cells of a cancer cell line into an immunodeficient mouse. The mice are then treated by intraperitoneal injection of antibodies and tumor size measured at regular intervals. Compared to control injections, antibodies of the invention inhibit tumor growth. In one embodiment, an antibody of the invention promotes tumor regression when combined with an anti-neoplastic agent. In a further embodiment, antibodies of the invention promote tumor regression when used in a monotherapy. Promoting tumor regression means that administration of an effective amount of antibody, or an effective amount of a combination of an antibody and a neoplastic agent results in a reduction in size or necrosis of the tumor. Tumor regression may can be measured as an average across a group of subjects undergoing a particular treatment regimen, or can be measured by the number of subjects in a treatment group in which tumors regress.

The antibodies of the invention may be isolated or purified by any method known in the art, including precipitation by ammonium sulfate or sodium sulfate followed by dialysis against saline, ion exchange chromatography, affinity or immuno-affinity chromatography as well as gel filtration or zone electrophoresis. A preferred method of purification for the antibodies of the current invention is Protein-A affinity chromatography.

DNA encoding human antibodies can be prepared by recombining DNA encoding human constant regions and variable regions, other than the CDRs, derived substantially or exclusively from the corresponding human antibody regions and DNA encoding CDRs derived from a human.

Suitable sources of DNA that encode fragments of antibodies include any cell, such as hybridomas and spleen cells that express the full-length antibody. The fragments may be used by themselves as antibody equivalents, or may be recombined into equivalents, as described above. The DNA deletion, recombination and other techniques described in this section may be carried out by known methods. Another source of DNA is a phage display library of antibodies, as is known in the art. The exemplified antibodies of the current invention were made via phage display technology.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2µ plasmid. Suitable vectors for expression in mammalian cells include well-known derivatives of SV-40, adenovirus, retrovirus-derived DNA sequences and shuttle vectors derived from combination of functional mammalian vectors, such as those described above, and functional plasmids and phage DNA.

Additional eukaryotic expression vectors are known in the art (e.g., P. J. Southern and P. Berg, J. Mol. Appl. Genet. 1:327-41 (1982); Subramani et al., Mol. Cell. Biol. 1:854-64 (1981); Kaufmann and Sharp, J. Mol. Biol. 159:601-21 (1982); Kaufmann and Sharp, Mol. Cell. Biol. 159:601-64 (1982); Scahill et al., Proc. Nat'l Acad. Sci. 80:4654-59 (1983); Urlaub and Chasin, Proc. Nat'l Acad. Sci. 77:4216-20 (1980)).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Where it is desired to express a gene construct in yeast, a suitable selection gene for use in yeast is the trp1 gene present in the yeast plasmid YRp7. Stinchcomb et al., Nature 282:39 (1979); Kingsman et al., Gene 7:141 (1979). The trp1 gene provides a selection marker for a mutant strain of yeast lacking the ability to grow in tryptophan, for example, ATCC No. 44076 or PEP4-1. Jones, Genetics 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The present invention also provides recombinant host cells containing the expression vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells. Suitable additional eukaryotic cells include yeast and other fungi. Useful prokaryotic hosts include, for example, *E. coli*, such as *E. coli* SG-936, *E. coli* HB 101, *E. coil* W3110, *E. coli* X1776, *E. coli* X2282, *E. coli* DHI, and *E. coli* MRC1, *Pseudomonas, Bacillus*, such as *Bacillus subtilis*, and *Streptomyces*.

These recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence (see, Shokri et al., Appl Microbiol Biotechnol. 60:654-64 (2003); Nielsen et al., Prot. Eng. 10:1-6 (1997); and von Heinje et al., Nucl. Acids Res. 14:4683-90 (1986)) at the 5' end of the antibody-encoding gene of interest. These secretory leader peptide elements can be derived from either prokaryotic or eukaryotic sequences. Accordingly, suitable secretory leader peptides are used, being amino acids joined to the N-terminal end of a polypeptide to direct movement of the polypeptide out of the host cell cytosol and secretion into the medium.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

The antibodies of this invention can be fused to additional amino acid residues. Such amino acid residues can be a peptide tag, perhaps to facilitate isolation. Other amino acid residues for homing of the antibodies to specific organs or tissues are also contemplated.

Another embodiment for the preparation of antibodies in the present invention is the expression of the nucleic acid encoding the antibody according to the invention in a transgenic animal that has a substantial portion of the human antibody producing genome inserted and is rendered deficient in the production of endogenous antibodies. Transgenic animals, include but not limited to mice, goat, and rabbit. One further embodiment of the invention includes expression of the antibody-coding gene in, for example, the mammary gland of the animal for secretion of the polypeptide during lactation.

As described in the examples below, high affinity anti-FLT3 antibodies according to the present invention can be isolated from a phage display library constructed from human heavy chain and light chain variable region genes. For example, a variable domain of the invention can be obtained from a peripheral blood lymphocyte that contains a rearranged variable region gene. Alternatively, variable domain portions, such as CDR and FW regions, can be derived from different human sequences. Over 90% of recovered clones after three rounds of selection are specific to FLT3. The binding affinities for FLT3 of the screened Fabs can be in the nM range, which is as high as many bivalent anti-FLT3 monoclonal antibodies produced using hybridoma technology.

Antibodies of the present invention can be obtained, for example, from naturally occurring antibodies, or Fab or scFv phage display libraries. Single domain antibodies can be obtained by selecting a VH or a VL domain from a naturally occurring antibody or hybridoma, or selected from a library of VH domains or a library of VL domains. It is understood that amino acid residues that are primary determinants of binding of single domain antibodies can be within Kabat or Chothia defined CDRs, but may include other residues as well, such as, for example, residues that would otherwise be buried in the VH-VL interface of a VH-VL heterodimer.

Antibodies of the present invention also include those for which binding characteristics have been improved by direct mutation, methods of affinity maturation, phage display, or chain shuffling. Affinity and specificity may be modified or improved by mutating CDRs and screening for antigen binding sites having the desired characteristics (see, e.g., Yang et al., J. Mol. Biol. 254:392-403 (1995)). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error-prone PCR methods (see, e.g., Hawkins et al., J. Mol. Biol. 226: 889-896 (1992)). For example, phage display vectors containing heavy and light chain variable region genes may be propagated in mutator strains of E. coli (see, e.g., Low et al., J. Mol. Biol. 250: 359-368 (1996)). These methods of mutagenesis are illustrative of the many methods known to one of skill in the art.

The protein used to identify FLT3 binding antibodies of the invention is preferably FLT3 and, more preferably, is the extracellular domain of FLT3. The FLT3 extracellular domain can be free or conjugated to another molecule.

The antibodies of this invention can be fused to additional amino acid residues. Such amino acid residues can be a peptide tag, perhaps to facilitate isolation. Other amino acid residues for homing of the antibodies to specific organs or tissues are also contemplated.

In another aspect of the invention, anti-FLT3 inhibitors, including but not limited to antibodies of the invention, can be administered in conjunction with, or chemically or biosynthetically linked to, anti-neoplastic or anti-angiogenic agents or detectable signal-producing agents. As exemplified below, antibodies of the invention are efficiently internalized upon binding to cells bearing FLT3. Anti-tumor agents administered in conjunction with, conjugated to, or linked to an antibody include any agents which destroy or damage a tumor to which the antibody has bound or in the environment of the cell to which the antibody has bound. In one aspect, an anti-FLT3 inhibitor, including the antibodies of the present invention, can be administered as a conjugate which binds specifically to the receptor and delivers a toxin following ligand-toxin internalization. In another aspect, a FLT3 inhibitor-agent conjugate can be directly linked to each other or joined via a linker, peptide or non-peptide. For example, an anti-tumor agent is a toxic agent such as a chemotherapeutic agent or a radioisotope. Suitable anti-neoplastic agents are known to those skilled in the art and include anthracyclines (e.g. daunomycin and doxorubicin), auristatin, methotrexate (MTX), vindesine, neocarzinostatin, cis-platinum, chlorambucil, cytosine arabinoside, 5-fluorouridine, melphalan, ricin and calicheamicin. The chemotherapeutic agents are conjugated to the inhibitor, antibody or small molecule using conventional methods (See, e.g., Hermentin and Seiler, Behring Inst. Mitt. 82:197215 (1988)). In one aspect, MTX is a preferred anti-neoplastic agent of the invention.

The invention further contemplates anti-FLT3 antibodies linked to target or reporter moieties, including by way of example only anti-neoplastic agents, other antibodies or reporters, such as radiolabled isotopes, in a diagnostic system where a detectable signal-producing agent is conjugated to the antibody.

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

The invention further contemplates anti-FLT3 antibodies to which target or reporter moieties are linked. Target moieties are first members of binding pairs. Anti-neoplastic agents, for example, are conjugated to second members of such pairs and are thereby directed to the site where the anti-FLT3 antibody is bound. A common example of such a binding pair is avidin and biotin. In a preferred embodiment, biotin is conjugated to an anti-FLT3 antibody, and thereby provides a target for an anti-neoplastic agent or other moiety, which is conjugated to avidin or streptavidin. Alternatively, biotin or another such moiety is linked to an anti-FLT3 antibody of the invention and used as a reporter, for example in a diagnostic system where a detectable signal-producing agent is conjugated to avidin or streptavidin.

Suitable radioisotopes for use as anti-tumor agents are also known to those skilled in the art. For example, $^{131}$I or $^{211}$At is used. These isotopes are attached to the antibody using conventional techniques (See, e.g., Pedley et al., Br. J. Cancer 68:69-73 (1993)). Alternatively, the anti-tumor agent which is attached to the antibody is an enzyme which activates a prodrug. In this way, a prodrug is administered which remains in its inactive form until it reaches the tumor site where it is converted to its cytotoxin form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques.

A method of treating tumor growth in a mammal by administering to the mammal an effective amount of an antibody as previously described is also provided by the present invention. Suitable conditions to be treated according to the present invention involve cells preferably expressing FLT3. While not intended to be bound to any particular mechanism, the present methods provide for treatment of the growth of cancer cells including for example, those in which neoplastic growth, organ transplant rejection or an immune disorder such as an autoimmune disease which is stimulated by FLT3.

"Treatment" or "treat", in the context of the present invention refers to therapeutic treatment including inhibiting, slowing, lessening or reversing the progress of the underlying condition or undesired physiological change associated with a disease or disorder, ameliorating clinical symptoms of a condition or preventing the appearance of clinical symptoms of the condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. "Treatment" can also mean prolonging survival as compared to expected survival if not receiving treatment. Those in need of treatment include those already with the disease. In one embodiment, the present invention can be used as a medicament.

One precancerous condition to be treated is myelodysplastic syndrome. Other cancers to be treated include but are not limited to hematological malignancies such as leukemia, i.e., AML, ALL and CML in blast crisis, among others. Other leukemias include those in Table 9, which lists the expression of FLT3 in selected human leukemia cell lines obtained from EB10 staining of selected leukemia cell lines. The cancer may also be a solid tumor, such as a thyroid or brain tumor.

In the methods of the present invention, a therapeutically effective amount of an antibody of the invention is administered to a mammal in need thereof. Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. The term administering as used herein means delivering the antibodies of the present invention to a mammal by any method that can achieve the result sought. They can be administered, for example, intravenously or intramuscularly. Although human antibodies of the invention are particularly useful for administration to humans, they can be administered to other mammals as well. The term mammal as used herein is intended to include, but is not limited to, humans, laboratory animals, domestic pets and farm animals. Therapeutically effective amount means an amount of antibody of the present invention that, when administered to a mammal, is effective in producing the desired therapeutic effect, such as inhibiting tumor growth. Treatment dosages may be titrated using routine methods known to those of skill in the art to optimize safety and efficacy.

The pharmaceutical compositions of the invention may include a "therapeutically effective amount" of an anti-FLT3 antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. Dosage regimens may be adjusted to provide the optimum desired response (e.g., a therapeutic or prophylactic response).

The present anti-FLT3 antibodies are administered for therapeutic treatments to a patient in need thereof in an amount sufficient to inhibit, or reduce the progression of the tumor or pathologic condition. Progression includes, e.g., the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. An exemplary, non-limiting range for a therapeutically effective amount of an antibody of the invention is 0.1-50 mg/kg, more preferably 3-35 mg/kg, and more preferably 5-20 mg/kg. Dosing amounts and frequencies will be determined by the physicians treating the patient and may include doses from less than 1 mg/kg to over 100 mg/kg given daily, three times per week, weekly, once every two weeks, or less often. Dose per administration may be in the range of 1-100, 2-75, or 5-60 mg/kg. It should be noted, however, that the present invention is not limited to any particular dose.

In alternative embodiments, the invention also includes methods of inhibiting dendritic cell activation or maturation comprising contacting the dendritic cell with an antibody of the invention either alone or in combination with other agents. Another method of the invention includes preventing organ transplant rejection or treating an autoimmune disease such as multiple sclerosis or encephalitis comprising administering the antibody of the invention alone or in combination with other agents.

In an embodiment of the invention, anti-FLT3 antibodies can be administered in combination with one or more other anti-neoplastic agents. For examples of combination therapies, see, e.g., U.S. Pat. No. 6,217,866 (Schlessinger et al., Anti-EGFR antibodies in combination with anti-neoplastic agents); WO 99/60023 (Waksal et al., Anti-EGFR antibodies in combination with radiation). Any suitable anti-neoplastic agent can be used, such as a chemotherapeutic agent, radiation or combinations thereof.

The anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents. Examples of alkylating agents include, but are not limited to, cisplatin, cyclophosphamide, melphalan, and dacarbazine. Examples of anti-metabolites include, but are not limited to, cytosine arabinoside, doxorubicin, daunorubicin, paclitaxel, gemcitabine, ALIMTA® and topoisomerase inhibitors irinotecan (CPT-11), aminocamptothecin, camptothecin, DX-8951f, topotecan (topoisomerase I), etoposide (VP-16), and teniposide (VM-26) (topoisomerase II). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

In one aspect of the present invention, MTX is the preferred anti-neoplastic agent to be given in combination with an antibody of the invention. Data provided herein demonstrate synergistic effects of the anti-FLT3 antibody, EB10, combined with MTX. This combination is particularly novel and unexpected given the in vitro work published by Furukawa et al. (Leukemia 21: 1005-1014 (2007)), which reported that simultaneous administration of a FLT3 inhibitor, PKC412, with other chemotherapeutic agents excluding MTX is clinically effective against FLT3 leukemia.

In the present invention, any suitable method or route can be used to administer anti-FLT3 antibodies of the invention, and optionally, to co-administer anti-neoplastic agents and/or antagonists of other receptors. In a combination therapy of the present invention, the anti-FLT3 antibody could be administered before, during, or after commencing therapy with another agent, including by of example only MTX, as well as any combination thereof, i.e., before and during, before and after, during and after, or before, during and after commencing the anti-neoplastic agent therapy. For example, the anti-FLT3 antibody can be administered between 1 and 30 days, preferably 3 and 20 days, more preferably between 5 and 12 days before commencing radiation therapy. In a preferred embodiment of the invention, chemotherapy is administered concurrently with or, more preferably, subsequent to antibody therapy.

In another aspect of the invention, any FLT3 inhibitor can used in combination with MTX for the treatment of leukemia.

Anti-FLT3 antibodies of the invention can be administered with antibodies that neutralize other receptors involved in tumor growth or angiogenesis. In an embodiment of the invention, an anti-FLT3 antibody is used in combination with a receptor antagonist that binds specifically to EGFR. Another example of such a receptor is VEGFR. An anti-FLT3 antibody of the present invention can be used in combination with a VEGFR antagonist. In an additional alternative embodiment, the FLT3 antibody can be administered in combination with one or more suitable adjuvants, such as, for example, cytokines (IL-10 and IL-13, for example) or other immune stimulators, such as, but not limited to, chemokine, tumor-associated antigens, and peptides. In addition, these stimulators can be administered with MTX. It should be appreciated, however, that administration of an anti-FLT3 antibody alone, as a monotherapy, is sufficient to prevent, inhibit, or reduce the progression of the tumor in a therapeutically effective manner.

In the present invention, any suitable method or route can be used to administer anti-FLT3 antibodies of the invention, and optionally, to co-administer anti-neoplastic agents such as MTX and/or antagonists of other receptors. The anti-neoplastic agent regimens utilized according to the invention, include any regimen believed to be optimally suitable for the treatment of the patient's neoplastic condition. Different malignancies, including various forms of leukemia can require the use of specific anti-tumor antibodies and specific anti-neoplastic agents, which will be determined on a patient to patient basis. Routes of administration include, for example, oral, intravenous, intraperitoneal, subcutaneous, intathecal, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

It is understood that the anti-FLT3 antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide rapid, sustained or delayed release of the active ingredient after administration to the mammal.

The present invention also includes kits for inhibiting tumor growth and/or angiogenesis comprising a therapeutically effective amount of a human anti-FLT3 antibody. Another embodiment of the present invention includes kits for inhibiting tumor growth and/or angiogenesis comprising a therapeutically effective amount of a human anti-FLT3 antibody with MTX. The kits can further contain any suitable antagonist of, for example, another growth factor receptor involved in tumorigenesis or angiogenesis (e.g., EGFR, VEGFR-1/Flt-1, VEGFR-2, PDGFR, NGFR, and FGFR). Alternatively, or in addition, the kits of the present invention can further comprise an anti-neoplastic agent. Examples of suitable anti-neoplastic agents in the context of the present invention have been described herein. The kits of the present invention can further comprise an adjuvant, examples of which have been described above.

Moreover, included within the scope of the present invention is the use of the present antibodies in vivo and in vitro for investigative or diagnostic methods, which are well known in the art. The diagnostic methods include kits, which contain antibodies of the present invention.

The antibodies of this invention bind to FLT3 with a binding strength stronger than that of FLT3 ligand binding activity, i.e., with a $K_D$ of about $200 \times 10^{-12}$ M to $500 \times 10^{-12}$ M. $K_D$ for antibody binding to a human FLT3-Fc fusion protein is from $0.5 \times 10^{-10}$ M to $5 \times 10^{-10}$ M determined at 25° C.; preferred antibodies bind to a human FLT3-Fc fusion protein with a $K_D$ from, $1.0 \times 10^{-10}$ M to $4.75 \times 10^{-10}$ M, $1.5 \times 10^{-10}$ M to $4.5 \times 10^{-10}$ M, or no greater than $4.5 \times 10^{-10}$ M, all determined at 25° C. It is preferred that the antibody binds to FLT3 with a dissociation rate constant ($K_d$ or $k_{off}$) between $4.5 \times 10^{-5}$ 1/s (sec$^{-1}$, 1/seconds) and $6 \times 10^{-5}$ 1/s, $5.0 \times 10^{-5}$ 1/s and $5.7 \times 10^{-5}$ 1/s, all as measured by surface plasmon resonance, described herein, at 25° C. and more preferably that antibody binds to FLT3 with a $K_d$ or $k_{off}$ between $5.1 \times 10^{-5}$ 1/s and $5.6 \times 10^{-5}$ 1/s, or within 10% of these rate constants. It is further preferred that the antibody binds to FLT3 with an association rate constant ($K_a$ or $k_{on}$) between $0.5 \times 10^{-5}$ M$^{-1}$sec$^{-1}$ (1/Ms; 1/molar 1/seconds) and $5 \times 10^5$ M$^{-1}$sec$^{-1}$, or $1 \times 10^5$ M$^{-1}$sec$^{-1}$ and $4 \times 10^5$ M$^{-1}$ sec$^{-1}$ all as measured by surface plasmon resonance, described herein, at 25° C. and more preferably that antibody binds to FLT3 with a $K_a$ or $k_{on}$ between $1.2 \times 10^5$ M$^{-1}$sec$^{-1}$ and $3.6 \times 10^5$ M$^{-1}$sec$^{-1}$, or within 10% of these rate constants. In a further embodiment, the antibody binds to FLT3 with a dissociation rate constant, as measured by surface plasmon resonance at 25° C., that is within 10% of the dissociation rate constant determined for EB10, NC7, or D4-3 under the same conditions.

The present invention comprises a monoclonal antibody, or fragment thereof, specific for FLT3 comprising one or more CDRs selected from the group consisting of the CDRs in Tables 1 and 2. In another aspect, the invention is a monoclonal antibody, or fragment thereof, specific for FLT3 having a light chain CDR3 region with the sequence: MQGTHPAIS (SEQ ID NO:9). In another aspect, the invention is a monoclonal antibody, or fragment thereof, specific for FLT3 having a heavy chain CDR3 with the sequence: GVGAHDAFDI (SEQ ID NO:4). In a different aspect, the invention is a monoclonal antibody, or fragment thereof, comprising (i) a light chain variable region selected from the group consisting of EB10, NC7, and D4-3 and (ii) a heavy chain variable region selected from the group consisting of EB10, NC7, and D4-3. In another aspect, the invention is a monoclonal antibody, or fragment thereof, specific for FLT3 comprising (i) a light chain variable region of EB10, NC7, and D4-3 (ii) a heavy chain variable region of EB10, NC7, and D4-3, and (iii) human immunoglobulin $G_1$ (hIgG$_1$) constant regions.

One aspect of the invention is an antibody, or fragment thereof, which binds an epitope of FLT3, wherein the epitope comprises up to five extracellular domains (D1, D2, D3, D4 and D5), and at a minimum comprises either or both domains D4 or D5. In a further aspect, the epitope is D4. In yet a further aspect, the epitope is D5.

In one embodiment of the present invention, the antibody or antibody fragment inhibits phosphorylation of a downstream pathway of FLT3 including STAT5, Akt, PI3K and MAPK.

In one aspect the presently disclosed antibodies are immunoconjugated to an antineoplastic agent including auristatin or methotrexate. The immunoconjugate can be linked to a detectable label. Another aspect is a method of detecting by contacting a target cell sample with the antibody or antibody fragment and determining if the sample contains FLT3 by detecting the labeled antibody.

In one aspect, the therapeutic composition is effective to inhibit growth of neoplastic cells that express FLT3 or promoting regression of human tumors that express FLT3. In further aspects, the therapeutic compositions are the presently disclosed antibodies and a pharmaceutically acceptable carrier.

Another aspect of the present invention is a method of neutralizing the activation of FLT3 within a mammal by administering to the mammal an effective amount of the antibody or antibody fragment thereof. Yet another aspect is a method of inhibiting dendritic cell activation or maturation comprising contacting the dendritic cell with the antibody or fragment presently disclosed in an amount effective to inhibit dendritic cell activation or maturation.

Another aspect of this invention is a method of treating cancer in a mammal comprising administering to the mammal an effective amount of an antibody, or fragment thereof, of any of the aspects already described. The invention also provides a method to treat hematological malignancies including leukemia. In this invention leukemia includes, but is not limited to: acute myeloid leukemia (AML), acute lymphocytic leukemia (ALL), chronic myeloid leukemia blast crisis (CML in blast crisis) and myelodysplastic syndrome. Another treatment method provided by this invention combines using the antibodies or fragments thereof of this invention along with administering an additional anti-cancer agent or treatment. In one treatment method, the anti-cancer agent is methotrexate (MXT).

Accordingly, the present receptor antibodies thus can be used in vivo and in vitro for investigative, diagnostic, prophylactic, or treatment methods, which are well known in the art. Variations in the principles of invention herein disclosed can be made by one skilled in the art and it is intended that such modifications are to be included within the scope of the present invention.

It is to be understood and expected that variations in the principles of invention herein disclosed can be made by one skilled in the art and it is intended that such modifications are to be included within the scope of the present invention.

The following examples further illustrate the invention, but should not be construed to limit the scope of the invention in any way; they should in no way be construed as limiting the broad scope of the invention. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J et al., Molecular Cloning: A Laboratory Manual, 2nd ed., Cold Spring Harbor Laboratory Press (1989) and Coligan, J. et al. Current Protocols in Immunology, Wiley & Sons, Incorporated (1994).

Expression and Purification of Human Anti-FLT3 Antibodies:

For each antibody, engineer a suitable heavy chain nucleotide sequence, for example SEQ ID NOs 37, 38, or 39 (for EB10, NC7 and D4-3 respectively) into a suitable expression plasmid, for example pGSHC, and engineer a suitable light chain nucleotide sequence, for example SEQ ID No. 40, 41, or 42 (for EB10, NC7 and D4-3 respectively) into a suitable expression plasmid, such as pGSLC, by a suitable method such as PCR cloning. To establish a stable cell line, co-transfect in a suitable host cell line, such as NSO or CHO cells, with linearized heavy and light chain plasmids by electroporation and culture in suitable media such as glutamine free Dulbecco's Modified Eagle Medium with dialyzed fetal calf serum and glutamine synthetase supplement. Screen clones for antibody expression by an enzyme-linked immunosorbent assay (ELISA) and select the highest producer for culture in spinner flasks. Purify antibodies by a suitable method such as protein-A affinity chromatography.

The present invention includes the recombinant human monoclonal antibody EB10, a full length IgG1κ targeting the human FLT3 receptor. It is comprised of a human gamma-1 heavy chain of subgroup I and a human kappa light chain of subgroup II. The EB10 Fab was isolated from a human Fab phage display library by selection for high affinity binding to the human FLT3 receptor and its ability to block ligand binding to the receptor. EB10 was shown to selectively bind to human FLT3 with high affinity, block FL binding and mediated potent anti-tumor activity in xenograft models by a mechanism involving activation of immune effector function.

The present invention also includes the recombinant human monoclonal antibody NC7, a full length IgG1κ targeting the human FLT3 receptor. It is comprised of a human gamma-1 heavy chain of subgroup I and a human kappa light chain of subgroup II. NC7 was shown to selectively bind to human FLT3 with high affinity and block FL binding.

The present invention also includes the recombinant human monoclonal antibody D4-3, a full length IgG1κ targeting the human FLT3 receptor. It is comprised of a human gamma-1 heavy chain of subgroup I and a human kappa light chain of subgroup II. D4-3 was shown to selectively bind to human FLT3 with high affinity and block FL binding.

Tables 1 and 2 provide the amino acid sequences and SEQ ID NOs of the various CDRs of the present invention. All CDR sequences are determined using the Kabat convention except for SEQ ID NOs 1 and 12, which were determined using the Chothia convention. Table 3 provides the SEQ ID NOs of the various sequences related to the present invention. Polynucleic acid sequences that encode the amino acid sequences disclosed below are also included within the scope of the present invention.

TABLE 1

Amino Acid Sequence of EB10 Antibody Heavy and Light Chain Variable Region CDRs.

|      | Heavy Chain        | SEQ ID NO. | Light Chain      | SEQ ID NO. |
|------|--------------------|------------|------------------|------------|
| CDR1 | GYTFTSYYMH<br>SYYMH | 1<br>2     | RSSQSLLHSNGNNYLD | 6          |
| CDR2 | IINPSGGSTSYAQKFQG  | 3          | LGSNRAS          | 8          |
| CDR3 | GVGAHDAFDI         | 4          | MQGTHPAIS        | 9          |

TABLE 2

Amino Acid Sequence of D4-3 Antibody Heavy and Light Chain Variable Region CDRs.

|      | Heavy Chain        | SEQ ID NO. | Light Chain      | SEQ ID NO. |
|------|--------------------|------------|------------------|------------|
| CDR1 | GYTFTSYYMH<br>SYYMH | 1<br>2     | RSSQSLLHSNGYNYLD | 7          |
| CDR2 | IINPSGGSTSYAQKFQG  | 3          | LGSNRAS          | 8          |
| CDR3 | VVAAAVADY          | 5          | MQSLQTPFT        | 11         |

TABLE 3

Amino Acid Sequence of NC7 Antibody Heavy and Light Chain Variable Region CDRs.

|      | Heavy Chain      | SEQ ID NO. | Light Chain | SEQ ID NO. |
|------|------------------|------------|-------------|------------|
| CDR1 | GGTFSSYAIS<br>SYAIS | 12<br>13 | RASQSISSYLN | 16         |
| CDR2 | GIIPIFGTANYAQKFQG | 14         | AASSLQS     | 17         |
| CDR3 | FALFGFREQAFDI    | 15         | QQSYSTPFT   | 18         |

TABLE 4

Amino Acid Sequence SEQ. ID. NOs of EB10, NC7 and D4-3 Antibodies

| | Heavy Chain | | | Light Chain | | |
|---|---|---|---|---|---|---|
| Antibody | Variable region | Complete Without signal | Complete With signal | Variable region | Complete Without signal | Complete With signal |
| EB10 | 19 | 25 | 31 | 22 | 28 | 34 |
| NC7  | 20 | 26 | 32 | 23 | 29 | 35 |
| D4-3 | 21 | 27 | 33 | 24 | 30 | 36 |

Antibodies used in experiments comprised full-length heavy and light chains without signals, as given in Table 4.

TABLE 5

Summary of In Vitro Data for EB10, NC7, and D4-3 Antibodies

| Antibody | FLT3 Binding ELISA (EC$_{50}$) | Ligand-receptor Binding Competition ELISA (IC$_{50}$) | FACS (MFI*) | Affinity $K_D$ (M) | Human ADCC (%) |
|---|---|---|---|---|---|
| EB10 | 0.5-1.0 nM | 0.5-1.0 nM | 54 | $1.58 \times 10^{-10}$ | 67% |
| NC7  | 0.3 nM     | 0.8 nM     | 63 | $4.5 \times 10^{-10}$  | 27% |
| D4-3 | 0.2 nM     | 7 nM       | 72 | $2.7 \times 10^{-10}$  | 7%  |

*FACS analysis was performed using EOL-1 leukemia cells as described below.
MFI = Mean Florescence Intensity Binding Epitope of Anti-FLT3 Antibodies Construct a series of FLT3 extracellular domain deletion mutants-Fc fusion by progressively deleting extracellular Ig domains of FLT3 from the C-terminus, resulting in the production of 5 constructs, including 4 truncated receptor proteins: FLT3-D1, FLT3-D1-2, FLT3-D1-3, FLT3-D1-4, and the full-length receptor, FLT3-D1-5. Generate a set of FLT3 ECD variants by serially deleting the Ig-like domains of the FLT3 ECD using a PCR-based strategy. Produce four deletion variants: Fd1 (amino acid 24-183), Fd1-2 (amino acid 24-271), Fd1-3 (amino acid 24-370), and Fd1-4 (amino acid 24-451). As the positive control, produce the full-length FLT3 (Fd1-5) containing amino acid 24-541 in a similar manner. Clone all the constructs into the expression vector pcDNA 3.1(+) (Invitrogen, Carlsbad, Calif.) using NheI and HindIII restriction sites where they ligate in-frame with the Fc domain of human IgG1 fused on C-terminus to a hexahistidine (His) tag. Verify the integrity of each of the constructs by DNA sequencing. Transiently express the constructs in COS cells, and verify by Western blot analysis the correct size of each expressed construct. Concentrate the cell culture supernatants. Examine binding of FL to the mutant receptors by estimating the relative protein concentration of each variant in the supernatant by both an anti-human Fc ELISA and by Western blot analysis and then adjust to approximately the same level before being used in the binding assay.

Analyze the binding of the FLT3 ECD domain deletion variants to FL and the antibodies by ELISA. Briefly, coat 96-well plates with an anti-His antibody (Qiagen), followed by incubation with the FLT3 ECD Ig domain deletion variants, as described above, for 1 hour with gentle shaking. Wash the plates 3 times with PBST (phosphate buffered saline with 0.1% TWEEN®-20), and then incubate with 100 µl/well of serial dilutions of the anti-FLT3 IgG antibodies in 2% M PBST. After 3 washes, incubate the plates with 100 µl/well of HRP-conjugated anti-human Fab antibody (Jackson ImmunoResearch Labs Inc.). In ligand binding assay, coat the plates with FL (100 ng/well) overnight at 4° C., followed by incubation with the FLT3 ECD Ig domain deletion variants for 1 hour with gentle shaking. After 3 washes, incubate the plates with 100 µl/well of HRP-conjugated anti-human Fc antibody (Jackson ImmunoResearch Labs Inc.). Develop the plates as described above. Examine binding of FL to the mutant receptors.

Epitope-mapping studies revealed that both EB10 and D4-3 monovalent Fab fragments, but not NC7 Fab, block FLT3 from binding to its ligand as shown by the fact that EB10 and D4-3 bind to FLT3-D1-4 (but not to FLT3-D1-3) and the full length receptor, thus mapping their binding epitope(s) within Ig domain 4 to which human FL also binds. On the other hand, NC7 only binds to the full-length receptor, but not to any other mutants, thus indicating its binding site is located within Ig domain 5. Accordingly, the antibodies of the present invention, bind domain 4 or domain 5 which is different than ligads known in the art which bind to domains 1 to 3.

Competition Enzyme-Linked Immunosorbent Assay (ELISA) and Blocking Assays

For the FLT3 binding assay, coat a 96-well plate was coated with an anti-His antibody (Qiagen, Hilden, Germany) overnight at 4° C. Block wells for 1 hour with blocking buffer (PBS containing 0.1% TWEEN-20® and 5% fetal calf serum (FCS)) and then incubate with FLT3-Fc (1 µg/mL×100 µl/well) for 1 hour at room temperature. Wash wells three times with PBST and then add EB10 or control IgG and incubated at room temperature for 1 hour. After washing, incubate the plate with 100 µl of anti-human kappa chain antibody-HRP conjugate at room temperature for 1 hour. Wash the plates and then incubate with 100 µl of 3,3', 5,5'-tetra-methylbenzidine. Use the microplate reader at the absorbance at 450 nm.

For the receptor-ligand blocking assay, mix varying amounts of EB10 or control IgG with a fixed amount of biotinated FLT3-Fc fusion protein (45 ng/well) and incubate at room temperature for 1 hour. Transfer the mixture to 96-well plates precoated with FL (25 ng/well) and then incubate at room temperature for an additional hour. After washing, add streptavidin HRP conjugate, and read the absorbance at 450 nm. Calculate the antibody concentration required for 50% inhibition of FLT3 binding to FL ($IC_{50}$).

The ability of EB10 to bind to the receptor was examined by ELISA. As shown in Table 6, EB10 binds FLT3 with an $EC_{50}$ within the range of 0.5-1 nM.

The ability of EB 10 to block receptor-ligand binding was examined in a FL binding competition ELISA. As shown in Table 7, EB10 blocked the binding of FL to FLT3 with an $IC_{50}$ within the range of 0.5-1 nM while no blocking activity was seen for control IgG.

TABLE 6

FLT3 Binding Activities of Anti-FLT3 Antibodies by Enzyme-Linked Immunosorbent Assay (ELISA)

| Antibody | Binding to FLT-3 ($EC_{50}$) |
|---|---|
| EB10 | 0.5-1.0 nM |
| NC7 | 0.3 nM |
| D4-3 | 0.2 nM |

TABLE 7

FLT3 Ligand-Receptor Blocking Activities of Anti-FLT3 Antibodies by Enzyme-Linked Immunosorbent Assay (ELISA)

| Antibody | Blocking of FL Binding to FLT-3 ($IC_{50}$) |
|---|---|
| EB10 | 0.5-1.0 nM |
| NC7 | 0.8 nM |
| D4-3 | 7 nM |
| IgG control | No blocking |

Accordingly, the antibodies of the present invention have high ligand blocking ability and high binding affinity for FLT3.

Binding Kinetics Analysis by Surface Plasmon Resonance/Biacore™ Analysis

Measure the binding kinetics of the antibody to FLT3 at 25° C. using the surface plasmon resonance, for example a Biacore 2000™ biosensor (Pharmacia Biosensor, Uppsala, Sweden) Immobilize approximately 1000 RU (reference units) of the antibody onto a sensor chip, and inject soluble FLT3-Fc fusion protein at concentrations ranging from 1.5~100 nM. Obtain sensorgrams at each concentration and evaluate using the instrument's program, for example BIA Evaluation 2.0 program, to determine the rate constants $k_{on}$ and $k_{off}$. $K_d$, also referred to as $k_{off}$, is the rate constant of the dissociation reaction. $K_a$, also referred to as $k_{on}$, is the rate constant of the association reaction. The affinity constant ($K_D$) is calculated from the ratio of rate constants $k_{on}$:$k_{off}$ measured in Molar (M). $K_a$, the $K_d$, and $K_D$ for the antibodies exemplified herein, EB10, NC7, and D4-3, are summarized in Table 8.

TABLE 8

Binding Kinetics of Antibodies to Recombinant Human FLT3

| Antibody | $K_a$ (1/Ms) $k_{on}$ | $K_d$ (1/s) $k_{off}$ | $K_D$ (M) |
|---|---|---|---|
| EB10 | $3.52 \times 10^5$ | $5.55 \times 10^{-5}$ | $1.58 \times 10^{-10}$ |
| NC7 | $1.24 \times 10^5$ | $5.6 \times 10^{-5}$ | $4.5 \times 10^{-10}$ |
| D4-3 | $1.9 \times 10^5$ | $5.1 \times 10^{-5}$ | $2.7 \times 10^{-10}$ |

Accordingly, the antibodies of the present invention have high binding kinetics for FLT3.

Flow Cytometric Analysis

Wash the various cells as listed below ($5 \times 10^5$ in 0.1 ml) twice in cold PBS and then incubate for 30 minutes with 10 µg/ml of anti-CD16/CD32 antibody (BD Pharmingen, San Diego, Calif.) in 100 µl PBS to block Fc receptors on the various cells (see Table 9). Wash cells with cold PBS and then incubate for 45 minutes with EB10 (10 µg/ml) or corresponding human IgG isotype control diluted in PBS. Wash cells with cold PBS and then incubate in 100 µl of PE-conjugated anti-human F(ab')2 secondary antibody (Jackson Immunoresearch) (1/200 dilution) for 45 minutes on ice. After washing, analyze cells by Flow Cytometery such as Coulter® Epics® Flow Cytometer (Beckman Coulter, Miami, Fla.); measure data in Mean Fluorescence Intensity (MFI).

Table 9 lists the results of EB10 staining of selected leukemia cell lines. Flow cytometric analysis showed that EB10 bound to wild-type FLT3 expressed on EOL-1 cells, and also to ITD-mutant FLT3 expressed on BaF3-ITD cells. No binding for EB10 was observed on the FLT3-negative JM1 or BaF3-control cell lines.

TABLE 9

EB10 Binding to FLT3 in Selected Human Leukemia Cell Lines by Flow Cytometery

| Tumor Cell Line | Leukemia Type | FLT3 Phenotype | MFI |
|---|---|---|---|
| BaF3/ITD | ALL | ITD mutant | 143.0 |
| EM-3 | CML | Wild type | 37.5 |
| EOL-1 | AML | Wild type | 53.5 |
| SEMK2 | ALL | Wild type | 526.3 |
| MOLM-14 | AML | Wild type/ITD (heterozygous) | 68.5 |
| MV-4-11 | Biphenotypic B myelomonocytic leukemia | ITD | 16.3 |
| OCI-AML5 | AML | Wild type | 24.3 |
| Reh | ALL | Wild type | 19.7 |
| RS4 | ALL | Wild type | 91.6 |
| JM1 | B cell lymphoma - leukemia | FLT3 negative | 0.1 |

Phosphorylation Assays

Culture cells in serum-free RPMI (Rosewell Park Memorial Institute) 1640 medium overnight. Treat cells for 60 minutes with various concentrations of antibodies in serum-free medium. Stimulate cells with 30 ng/ml FL for 15 minutes at 37° C. Lyse cells in lysis buffer (50 mM Tris, 150 mM NaCl, 1% NP-40, 1 mM EDTA, 1 mM phenylmethyl sulfonyl fluoride, 0.5 mM sodium orthovanadate, 1 µg/ml leupeptin, 1 µg/ml pepstatin A, and 1 µg/ml aprotinin). Incubate equal amounts of cell lysates from each sample overnight at 4° C. with anti-FLT3 antibody 4G8 (BD Pharmingen) and then with protein A agarose (Upstate Biotechnology, Lake Placid, N.Y.) for an additional 2 hours. After electrophoresis, transfer to nitrocellulose membranes (Invitrogen), perform immunoblotting with anti-phosphotyrosine antibody 4G10 (Upstate Biotechnology) to assess phosphorylated FLT3. Strip membranes treated with Qentix™ signal enhancer (Pierce, Rockford, Ill.) and re-probe with anti-FLT3 antibody S-18 (Santa Cruz Biotechnology, Santa Cruz, Calif.) to detect total FLT3 protein. Visualize protein bands were using chemiluminescence (Amersham, Piscataway, N.J.). To detect activated MAPK, Stat5 or AKT, separate 50 µg of cell protein extract by SDS-PAGE electrophoresis, transfer to nitrocellulose membranes, and immunoblot with indicated antibodies: Phospho-p44/42 MAPK antibody, Phospho-Stat5 (Cell Signaling Technology, Beverly, Mass.), or Phospho-AKT antibody (BD Pharmingen). To detect total MAPK, Stat5 or AKT proteins, strip membranes and re-probe with indicated antibodies: p44/42 MAPK antibody, Stat5 antibody (Cell Signaling Technology), or AKT antibody (BD Pharmingen).

EB 10 Inhibits FL-Induced Phosphorylation of Wild-Type FLT3 and Ligand-Independent Constitutive Phosphorylation of ITD-Mutant FLT3: In EOL-1 and EM3 cells, FL addition strongly increased FLT3 receptor phosphorylation. Incubation with EB10 blocked FL-induced phosphorylation in a dose-dependent manner with an $IC_{50}$ of 0.4–4 nM. These results indicate that EB10 is a potent inhibitor of ligand-induced activation of wild-type FLT3.

The ITD mutation found with high frequency in AML is known to cause FL-independent receptor phosphorylation and activation of kinase signaling pathways. EB10's inhibitory effect on constitutive activation of mutant FLT3 using BaF3-ITD and MV4;11 cell lines is reported in Table 10. The mutant FLT3 in both BaF3-ITD and MV4;11 cell lines was constitutively phosphorylated. In comparison to the control antibody, EB10 inhibited FL-independent FLT3-ITD phosphorylation in BaF3-ITD cells. To a lesser extent, EB10 also significantly inhibited FL-independent FLT3-ITD phosphorylation in MV4;11 cells. Taken together, these results demonstrate that EB10 is also a potent inhibitor of FLT3-ITD kinase activity.

TABLE 10

EB10 Inhibits FL-Induced Phosphorylation of Wild-Type FLT3 and Ligand-Independent Constitutive Phosphorylation of ITD-Mutant FLT3:

| Cell line | FLT3 Mutation Status | Inhibition of FLT3 Phosphorylation ($IC_{50}$) |
|---|---|---|
| EOL-1 | wild type | 0.4 nM |
| EM3 | wild type | 4 nM |
| BaF3-ITD | ITD mutation | 4 nM |
| MV4; 11 | ITD mutation | 40 nM |

The antibodies of the present invention inhibit FL-induced phosphorylation of wild-type FLT3.

EB10 Inhibits FLT3-Mediated Activation of Downstream Kinases: The MAPK, PI3K and Stat5 pathways have been identified to be involved in the downstream signaling of activated FLT3 (Stirewalt D L and J P, Radich, J P. Nat Rev Cancer 3:650-665 (2003)). The antibodies of the present invention inhibit downstream kinases of MPK, PI3K, and STAT5 pathways in leukemia.

The effect of EB 10 on FL-independent MAPK phosphorylation induced by the FLT3-ITD mutation was investigated using BaF3-ITD and MV4;11 cells. EB10 strongly blocked the phosphorylation of MAPK in both cell lines. These results demonstrate that blockade of the FLT3 ligand-receptor interaction by EB10 results in inhibition of the downstream MAPK signaling pathway (Table 11). Incubation with EB10 inhibited FL-induced phosphorylation of AKT in EOL-1 cells and FL-independent phosphorylation of AKT in BaF3-ITD cells (Table 12). In BaF3-ITD cells, FL-independent Stat5 phosphorylation was strongly inhibited by EB10, while in EOL-1 there was no effect (Table 13).

TABLE 11

EB10 Inhibits FLT3-Mediated Activation of Downstream Kinases MAPK

| Cell line | FLT3 Mutation Status | Inhibition of MAPK Phosphorylation ($IC_{50}$) |
|---|---|---|
| EOL-1 | wild type | 0.1 nM |
| EM3 | wild type | 0.1 nM |
| BaF3-ITD | ITD mutation | 0.1 nM |
| MV4; 11 | ITD mutation | 0.4 nM |

TABLE 12

Effect of EB10 on the phosphorylation of AKT

| Cell line | FLT3 Mutation Status | Inhibition of AKT Phosphorylation ($IC_{50}$) |
|---|---|---|
| EOL-1 | wild type | 1 nM |
| BaF3-ITD | ITD mutation | 0.1 nM |

TABLE 13

EB10 Inhibits FL-independent Stat5 phosphorylation

| Cell line | FLT3 Mutation Status | Inhibition of Stat5 Phosphorylation ($IC_{50}$) |
|---|---|---|
| EOL-1 | wild type | No effect |
| BaF3-ITD | ITD mutation | 4 nM |

Cell Proliferation Assays

Harvest EOL-1 cells and wash three times using serum-free RPMI 1640 medium. Culture cells in serum-free RPMI 1640 medium for 12 hours. For BaF3-ITD cells, perform the proliferation assay in RPMI 1640 medium supplemented with 10% FCS in the absence of exogenous FL. Reconstitute cells in serum-free AIM-V medium, plate in triplicates in a flat-bottomed 96-well plate ($1 \times 10^4/100$ µl/well) and incubate with varying concentrations of antibodies (from 0 to 100 nM) and 30 ng/ml of FL at 37° C. for 68 hours. As a background control, incubate cells with medium alone in the absence of exogenous FL. Pulse cells with 0.25 µCi/well of [$^3$H]-thymidine for 4 hours. Harvest cells and measure cpm in a PerkinElmer Wallace-1205 Betaplate Liquid Scintillation Counter (Wellesley, Mass.). Calculate the percent inhibition of FL-induced proliferation for EOL-1 cells; deduce the cpm of background proliferation (i.e., cell samples not stimulated with FL) from the cpm of all experimental samples. Calculate percent inhibition using the following formula: [(cpm of untreated sample—cpm of antibody-treated sample)/cpm of untreated sample]×100%.

EB10 Inhibits Proliferation of Leukemia Cells Expressing Wild-Type: FL plays an important role in the proliferation of leukemia cells. Incubation with FL increased the [3H]-thymidine uptake of EOL-1 cells. Treatment with EB10 inhibited FL-induced proliferation of EOL-1 cells in a dose-dependent manner (Table 14).

TABLE 14

EB10 Inhibits FL-induced Proliferation of EOL-1 Leukemia Cells

| Treatment | Concentration (nM) | % Inhibition of FL-induced proliferation (Mean ± Stardard deviation) |
|---|---|---|
| EB10 | 1.5 | 12.4 ± 2.1 |
| EB10 | 3 | 19.4 ± 1.8 |
| EB10 | 6 | 29.3 ± 6.5 |
| EB10 | 13 | 32.9 ± 1.7 |
| EB10 | 25 | 37.2 ± 7.2 |
| EB10 | 50 | 40.3 ± 11.5 |
| EB10 | 100 | 51.8 ± 8.2 |
| Control IgG | 100 | 0.4 ± 0.1 |

EB10 Inhibits Proliferation of Leukemia Cells Expressing ITD-Mutant FLT3: FLT3-ITD transformed BaF3 cells proliferate in the absence of FL stimulation. FL stimulation did not increase the proliferation of BaF3-ITD cells. EB10 treatment inhibited FL-independent proliferation of these cells in a dose-dependent manner (Table 15).

TABLE 15

EB10 Inhibits FL-induced Proliferation of BaF3 Leukemia Cells

| Treatment | Concentration (nM) | % Inhibition of FL-independent proliferation (Mean ± Standard deviation) |
|---|---|---|
| EB10 | 1.5 | 0.5 ± 2.4 |
| EB10 | 3 | 0.5 ± 5.6 |
| EB10 | 6 | 9.6 ± 3.1 |
| EB10 | 13 | 13.0 ± 4.0 |
| EB10 | 25 | 23.3 ± 0.6 |
| EB10 | 50 | 28.6 ± 3.1 |
| EB10 | 100 | 29.2 ± 3.0 |
| Control IgG | 100 | 2.0 ± 4.0 |

Antibody Internalization Assay

Radio-iodinate antibodies with $^{125}$I using IODO-beads (Pierce Biotechnology, Rockford, Ill., USA) according to the manufacturer's instructions. Aliquot EOL-1 cells into microfuge tubes at $5 \times 10^5$ cells/sample in 500 ml cold complete media. Add approximately 1 mg of EB10 and D4-3 $^{125}$I-labeled antibody to the cells and incubate for 1 hour at 4° C. Wash cells twice in cold PBS, resuspend in 500 ml complete media, then incubate at 4 or 37° C. for 0, 30, 60, 120, 240, or 360 minutes. At each time point, wash cells three times in PBS, then count the 4° C. samples on a gamma counter to determine the total amounts of radioactivity bound to the cell surface. Strip the 37° C. samples for 5 minutes with strip buffer (100 mM glycine, 2M urea, pH 2.5). Count both the stripping buffer and stripped cell pellets on a gamma counter to determine the percentage of radioactivity internalized.

TABLE 16

Internalization of anti-FLT3 Antibodies Bound to FLT3 on EOL-1 Cell Surface

| Antibody | Time at 37° C. (minutes) | % of antibody internalized (±SD) |
|---|---|---|
| EB10 | 0 | 11.1 (9.2) |
| | 30 | 40.5 (13.2) |
| | 60 | 55.0 (19.1) |
| | 120 | 53.9 (10.3) |
| | 240 | 79.9 (24.9) |
| | 360 | 50.4 (8.5) |
| D4-3 | 0 | 6.3 (5.1) |
| | 30 | 30.1 (4.9) |

TABLE 16-continued

Internalization of anti-FLT3 Antibodies
Bound to FLT3 on EOL-1 Cell Surface

| Antibody | Time at 37° C. (minutes) | % of antibody internalized (±SD) |
|---|---|---|
|  | 60 | 52.2 (1.7) |
|  | 120 | 59.5 (7.3) |
|  | 240 | 60.4 (4.9) |
|  | 360 | 68.5 (17.1) |

EOL-1 cells, radiolabeled with EB10 or D-43, readily bound to the surface of tumor cells and were internalized in a time dependent fashion (Table 16).

Antibody Dependent Cellular Cytotoxicity (ADCC) Against Human Leukemia In Vitro

Conduct ADCC assays by the standard $^{51}$Cr release assay. Obtain an enrichment of human natural killer (NK) cells from normal donor blood, such as from RosettaSep NK Cell Enrichment Cocktail; StemCell Technologies, Inc., Vancouver, British Columbia, Canada, or NK Cell Isolation Kit II, MiltenyiBiotec. Label target cells ($2\times10^6$) with 200 μCi $^{51}$Cr for 2 hours and then wash. Incubate the increasing numbers of NK cells (0 to 400,000 cells), which were previously incubated with 10 μg/mL (67 nmol/L) control IgG, C225, EB10, NC7 or D4-3 mAb for 45 minutes, with ~4,000 $^{51}$Cr-labeled target cells, in triplicate in V-bottomed 96-well plates for 6 hours at 37° C., or with 5% SDS to measure total lysis. For measuring spontaneous release, incubate targets cells (4,000 cells in 100 μl/well) with 100 μl medium only. Collect from each well supernatant of the cytotoxicity cultures and count $^{51}$Cr on a gamma counter (such as 1470 Wallac WIZARD, PerkinElmer Life and Analytical Sciences, Inc., Boston, Mass.). Calculate percent lysis or percent cytotoxicity as 100×(sample release—spontaneous release)/(total release—spontaneous release).

Unlike small molecule FLT3 inhibitors, antibodies to FLT3 may initiate patient immune responses towards FLT3 expressing tumor cells. In particular, antibodies can induce cell lysis if FLT3 expressing cells are coated with human IgG. This lysis can be the result of the activation of leukocytes, in particular Fc receptor expressing natural killer (NK) cells. The antibodies of the present invention provide human anti-FLT3 antibodies which have an improved ability to activate downstream immune effector functions such as ADCC. EB10 induced a strong ADCC response; NC7 and D4-3 induced a less potent ADCC response (Table 17).

TABLE 17

ADCC Human Leukemia Cells FLT3 In Vitro

| | % Cytotoxicity | | |
|---|---|---|---|
| E:T Ratio | EB10 | NC7 | D4-3 |
| 100:1 | 67 | 27 | 7 |
| 33:1 | 47 | 8 | 1 |
| 11:1 | 32 | 7 | 0 |
| 4:1 | 22 | 1 | 0 |

EB10, NC7 and D4-3 Effectively Treat Leukemia Xenografts

EOL-1 Xenograft Human AML Leukemia Model: Intravenously (i.v.) inject NOD-SCID mice in groups of 10 with $5\times10^6$ leukemia cells. Start treatment one day after tumor injection. Treat mice three times weekly with an intraperitoneal (i.p.) injection of indicated amounts of 500 μg, 250 μg or 100 μg/dose of EB10 in 200 μl phosphate buffered saline (PBS). Treat the control group with purified human IgG (500 μg/dose). Monitor mice daily for survival. Compare survival in the treatment groups by Log Rank test.

All mice in the control group succumbed to extensive dissemination of disease within 40 days (mean survival time 36.0±3.1 days). In comparison, survival was significantly prolonged in groups of mice treated with 500 μg, 250 μg or 100 μg/dose of EB10 (mean survival time 62.3±18.7, 55.3±18.9, or 52.8±18.6, with a P value of <0.001, <0.005, or <0.001, respectively). No effect was observed in the group treated with 10 μg of EB10, indicating that the anti-leukemic effect of EB10 was dose-dependent.

Bone Marrow Engraftment of Human Leukemia Cells: Harvest bone marrow from the femurs of EB10-treated mice (500 μg/dose) and the control-IgG treated group at day 20. Analyze cells for human CD45 by flow cytometry at 6 and 14 weeks post leukemia cell injection for the degree of tumor cell infiltration of bone marrow. Compare the degree of tumor cell infiltration of bone marrow using immunohistochemical staining with a fluorescence-labeled anti-human CD45 antibody. The number of tumor cells in bone marrow was decreased significantly in EB10-treated mice.

BaF3-ITD Leukemia Model: Initiate i.v. injection of groups of 10 athymic (nu/nu) mice with $5\times10^4$ BaF3-ITD cells. For statistic analysis, use the non-parametric one-tailed Mann-Whitney Rank Sum test (SigmaStat 2.03, SPSS, Inc., Chicago, Ill.). Start treatment one day after tumor injection. Treat mice three times weekly with an i.p. injection of 500 μg/dose or 100 μg/dose of EB10 in 200 μl PBS. Treat the control group with purified human IgG (500 μg/dose). Monitor mice daily for survival.

In comparison to control IgG treatment (mean survival time 32.4±10.6 days), EB10 treatment significantly prolonged the survival of mice (63.4±44.6 days, P<0.05 for the 500 μg dose, and 66.5±32.9 days, P<0.01 for the 100 μg dose). These results show that EB 10 is therapeutically effective in both wild-type FLT3 and ITD-mutant FLT3 models in vivo.

MOLM14 Xenograft AML Leukemia Model: Irradiate mice with 200 rads with a gamma irradiator and then i.v. inject with $10\times10^6$ MOLM-14 leukemia cells. Start treatment one day after tumor injection. Treat mice two times weekly with an i.p. injection of 10 mg/kg and 0.2 mg/kg doses of EB10 in 200 μl PBS. Treat the control group with 10 μg/ml USP saline. Monitor mice daily for survival. Compare survival in the treatment groups by Log Rank test.

EB10 significantly prolonged survival. Median survivals ranged from 63 days to 38.5 days for the 10 mg/kg and 0.2 mg/kg doses, respectively, compared to 36 days for the saline control. This effect was dose dependent, with each dose being significantly more efficacious than the next lower dose.

SEM-K2 Xenograft Human Leukemia Model: Initiate i.v. injection of NOD-SCID mice in groups of 10 with $5\times10^6$ leukemia cells. Start treatment one day after tumor injection. Treat mice two times weekly with an i.p. injection of 20 mg/kg of EB10, NC7 and D4-3 in 200 μl PBS. Treat the control group with purified human IgG (500 μg/dose). Monitor mice daily for survival. Compare survival in the treatment groups by Log Rank test.

The in vivo efficacy of EB10, NC7 and D4-3 was determined in SEM-K2 cells, a human ALL cell line expressing wild type FLT3. In comparison to human IgG (median survival 30.5 days), EB10, NC7 and D43 treatments all significantly prolonged survival (median survival 108.5 days, p<0.0001; 58.5 days, p<0.0001 and 55.5 days, p=0.0001, respectively) in the SEM-K2 leukemia model. The efficacy is significantly stronger for EB10 than for NC7 (p<0.0001) and D43 (p<0.0001). There is no significant difference in efficacy between NC7 and D43 (p=0.244).

EB 10 Efficacy Determined by PK Studies

In Repeat-Dose PK Studies EB10 was shown to be efficacious at very low doses. The threshold for maximum efficacy was found to be between 2 and 10 μg/ml. EB10 achieves maximal efficacy in murine leukemia models between 41 and 401 μg/ml Cavg, and between 49 and 475 μg/ml Cmax. A secondary range for Cmax is 375 to 475 μg/ml.

Combination Therapy with EB 10 and Chemotherapeutic Agent Methotrexate (MTX) in SEM-K2 Leukemia Model One day prior to the start of treatment, i.v. inject 65, 7 weeks old, male NOD/SCID mice with $5 \times 10^5$ SEM-K2 cells suspended in PBS in a total volume of 200 μl. Drop from the study mice receiving less than 90% of cells intravenously. The following day, divide the NOD-SCID mice bearing SEM-K2 leukemia cells into 4 treatment groups of 12 mice/group:

1) USP Saline 10 μl/gram, i.p., 2×/week;
2) EB10 10 mg/kg, i.p. 2×/week;
3) MTX 100 mg/kg, Q7D; and
4) Combination of MTX 100 mg/kg and EB 10 10 mg/kg.

Prepare MTX (Sigma Chemical, Cat # M9929) in USP Saline at a concentration of 10 mg/ml and dose Q7D for three cycles. Prepare EB10 in USP Saline and dosed 2×/week until day 40, when the last saline control animal died. Dose all mice at 10 ml/kg i.p. In the combination group, dose MTX at least one hour before EB 10 treatment starting on day 1. Record mouse survival daily. Follow the mice for survival, and sacrifice any mouse displaying signs of morbidity/mortality; mark as dead on the day of sacrifice. End the study on day 168 and sacrifice any mice surviving to that point. Compare survival in the treatment groups by Log Rank Test between treatment groups.

The effect of the combination of MTX, administered at its maximum tolerated dose, and EB10 on the survival of mice in a SEM-K2 model of ALL was determined SEM-K2 leukemia grew aggressively with all mice in the control group succumbing to leukemia by 34 days. Both EB10 and MTX were efficacious in this model, but the combination of the two agents had an effect significantly greater than either treatment as a monotherapy. EB10 therapy significantly prolonged mouse survival (p <0.01) in comparison to the control group. To a lesser extent, MTX therapy also prolonged survival.

Combination therapy with both EB10 and MTX had enhanced efficacy (P<0.001) in comparison to monotherapies. The combination of EB10 and MTX resulted in a significantly longer median survival than any other treatments in this model. In addition, four mice in the combination group survived to the end of the study, day 168, whereas no mice receiving other treatments survived to that point. The fact that combination treatment allowed some mice to survive beyond 150 days of treatment, whereas neither EB10 nor MTX as monotherapy were able to achieve this longevity demonstrates that the combination of EB10 and MTX is synergistic. This result is particularly unexpected given the in vitro work published by Furukawa et al. (Leukemia 21:1005-1014 (2007)), which reported that simultaneous administration of a FLT3 inhibitor, PKC412, with other chemotherapeutic agents excluding MTX is clinically effective against FLT3 leukemia.

---

We claim:

1. An antibody that specifically binds human FLT3 (SEQ ID NO. 43) or a FLT3-binding fragment of the antibody, comprising a CDRH1 having the sequence SYYMH (SEQ ID NO:2), a CDRH2 having the sequence IINPSGGSTSYAQK-FQG (SEQ ID NO:3), a CDRH3 having the sequence GVGAHDAFDI (SEQ ID NO:4) or VVAAAVADY (SEQ ID NO:5), a CDRL1 having the sequence RSSQSLLHSNGN-NYLD (SEQ ID NO:6) or RSSQSLLHSNGYNYLD (SEQ ID NO:7), a CDRL2 having the sequence LGSNRAS (SEQ ID NO:8), and a CDRL3 having the sequence MQGTHPAIS (SEQ ID NO:9) or MQSLQTPFT (SEQ ID NO:11).

2. The antibody or fragment of claim 1 comprising a CDRH1 having the sequence SYYMH (SEQ ID NO:2), a CDRH2 having the sequence IINPSGGSTSYAQKFQG (SEQ ID NO:3), a CDRH3 having the sequence GVGAH-DAFDI (SEQ ID NO:4), a CDRL1 having the sequence RSSQSLLHSNGNNYLD (SEQ ID NO:6), a CDRL2 having the sequence LGSNRAS (SEQ ID NO:8), and a CDRL3 having the sequence MQGTHPAIS (SEQ ID NO:9).

3. The antibody or fragment of claim 2, comprising a VL comprising the amino acid sequence:

```
                                           (SEQ ID NO: 22)
DVVMTQSPLSLPVTPGEPASISCRSSQSLLHSNGNNYLDWYLQKPGQSPQ

LLIYLGSNRASGVPDRFSGSGSDTDFTLQISRVEAEDVGVYYCMQGTHPA

ISFGQGTRLEIK,
``` and a VH comprising the amino acid sequence:

```
                                           (SEQ ID NO: 19)
EVQLVQSGAEVKKPGASVKVSCKASGYTFTSYYMHWVRQAPGQGLEWMGI

INPSGGSTSYAQKFQGRVTMTRDTSTSTVYMELSSLRSEDTAVYYCARGV

GAHDAFDIWGQGTTVTVSS.
```

4. The antibody of claim 3, comprising a light chain of SEQ ID NO: 28, and a heavy chain of SEQ ID NO: 25, or a FLT3-binding fragment of the antibody.

5. The antibody of claim 4, comprising two light chains of SEQ ID NO: 28 and two heavy chains of SEQ ID NO: 25, or a FLT3-binding fragment of the antibody.

6. A pharmaceutical composition comprising the antibody of claim 4 and a pharmaceutically acceptable carrier, diluent or excipient.

7. An antibody of claim 4 chemically or biosynthetically linked to an anti-neoplastic agent, an anti-angiogenic agent or a detectable signal-producing agent.

8. An antibody of claim 4 conjugated to an anti-tumor agent, wherein said agent can destroy or damage a tumor to which the antibody has bound or which is in the environment of the cell to which the antibody has bound.

9. The antibody or fragment of claim 1, comprising a CDRH1 having the sequence SYYMH (SEQ ID NO:2), a CDRH2 having the sequence IINPSGGSTSYAQKFQG (SEQ ID NO:3), a CDRH3 having the sequence VVAAA-VADY (SEQ ID NO:5), a CDRL1 having the sequence RSSQSLLHSNGYNYLD (SEQ ID NO:7), a CDRL2 having the sequence LGSNRAS (SEQ ID NO:8), and a CDRL3 having the sequence MQSLQTPFT (SEQ ID NO:11).

10. The antibody or fragment of claim 9, comprising a VL comprising the amino acid sequence:

```
                                           (SEQ ID NO: 24)
DVVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQSLQTP

FTFGPGTKVDIK,
``` and a VH comprising the amino acid sequence:

```
                                           (SEQ ID NO: 21)
EVQLVQSGAEVKKPGASVKVSCKASGYTFTSYYMHWARQAPGQGLEWMGI

INPSGGSTSYAQKFQGRVTMTRDTSTSTVYMELSSLRSEDTAVYYCARVV

AAAVADYWGQGTLVTVSS.
```

11. The antibody of claim 10, comprising a light chain of SEQ ID NO: 30, and a heavy chain of SEQ ID NO: 27, or a FLT3-binding fragment of the antibody.

12. The antibody of claim 11, comprising two light chains of SEQ ID NO:30 and two heavy chains of SEQ ID NO: 27, or a FLT3-binding fragment of the antibody.

13. An antibody that specifically binds human FLT3 (SEQ ID NO:43) or a FLT3-binding fragment of the antibody, comprising a CDRH1 having the sequence SYAIS (SEQ ID NO:13), a CDRH2 having the sequence GIIPIFGTAN-YAQKFQG (SEQ ID NO:14), a CDRH3 having the sequence FALFGFREQAFDI (SEQ ID NO:15), a CDRL1 having the sequence RASQSISSYLN (SEQ ID NO:16), a CDRL2 having the sequence AASSLQS (SEQ ID NO:17), and a CDRL3 having the sequence QQSYSTPFT (SEQ ID NO:18).

14. The antibody or fragment of claim 13, comprising a VL comprising the amino acid sequence:

```
                                           (SEQ ID NO: 23)
DIQMTQSPSSLSASVGDRVTITCRASQSISSYLNWYQQKPGKAPKLLIYA

ASSLQSGVPSRFSGSGSGTDFTLTISSLQPEDLATYYCQQSYSTPFTFGP

GTKVDIK,
``` and a VH comprising the amino acid sequence:

```
                                                (SEQ ID NO: 20)
EVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCATFA

LFGFREQAFDIWGQGTTVTVSS.
```

15. The antibody of claim 14, comprising a light chain of SEQ ID NO: 29, and a heavy chain of SEQ ID NO: 26, or a FLT3-binding fragment of the antibody.

16. The antibody of claim 15, comprising two light chains of SEQ ID NO: 29 and two heavy chains of SEQ ID NO: 26, or a FLT3-binding fragment of the antibody.

17. An isolated polynucleotide comprising a sequence encoding a light chain of SEQ ID NO: 28 or a heavy chain of SEQ ID NO: 25.

18. An expression vector comprising the polynucleotide of claim 17 operably linked to expression control elements such that an antibody comprising a light chain of SEQ ID NO: 28, and a heavy chain of SEQ ID NO: 25 may be expressed.

19. A recombinant mammalian cell comprising the expression vector of claim 18, which recombinant cell is capable of producing an antibody comprising a light chain of SEQ ID NO: 28, and a heavy chain of SEQ ID NO: 25.

20. A process for producing an antibody comprising a light chain of SEQ ID NO: 28, a heavy chain of SEQ ID NO: 25, comprising culturing the cell of claim 19 under conditions such that the antibody is expressed, and isolating the antibody.

21. An antibody or fragment produced by the process of claim 20.

22. A pharmaceutical composition comprising the antibody of claim 21 and a pharmaceutically acceptable carrier, diluent or excipient.

23. A method of treating cancer in a patient comprising administering to the patient an effective amount of the antibody or fragment of claim 4.

24. The method of claim 23, wherein the cancer is leukemia.

25. The method of claim 23, further comprising administering an effective amount of another anti-neoplastic agent or providing another anti-neoplastic treatment to the patient.

26. The method of claim 25, wherein the anti-neoplastic treatment comprises administering an effective amount of methotrexate.

* * * * *

UNITED STATES PATENT AND TRADEMARK OFFICE
CERTIFICATE OF CORRECTION

PATENT NO.        : 8,071,099 B2                                Page 1 of 1
APPLICATION NO.   : 12/890793
DATED             : December 6, 2011
INVENTOR(S)       : Yiwen Li et al.

It is certified that error appears in the above-identified patent and that said Letters Patent is hereby corrected as shown below:

Issued Patent

|          | Column | Line  | Description of Error |
|----------|--------|-------|----------------------|
| Claim 17 | 80     | 4     | In Claim 20, insert -- and -- prior to "a heavy". |
| Claim 21 | 80     | 13-15 | Delete Claim 23 in its entirety. |
| Claim 22 | 80     | 16-17 | Delete Claim 24 in its entirety. |
| Claim 23 | 80     | 18-20 | Delete Claim 25 in its entirety. |
| Claim 24 | 80     | 21-23 | Delete Claim 26 in its entirety. |
| Claim 25 | 80     | 61    | In Claim 7, delete "An" and insert -- The --, therefor. |
| Claim 26 | 80     | 64    | In Claim 8, delete "An" and insert -- The --, therefor. |

Signed and Sealed this
Fourth Day of September, 2012

David J. Kappos
*Director of the United States Patent and Trademark Office*